US012629487B2

(12) United States Patent
Sterke et al.

(10) Patent No.: US 12,629,487 B2
(45) Date of Patent: May 19, 2026

(54) INSUFFLATOR FOR EXPOSING STRUCTURES WITHIN AN INTERNAL BODY CAVITY

(71) Applicants: Erasmus University Medical Center Rotterdam, Rotterdam (NL); Politecnico di Milano, Milan (IT)

(72) Inventors: Frank Sterke, Eindhoven (NL); Willem Van Weteringen, Rotterdam (NL); Johnny Vlot, Rijswijk (NL); Tomas Gijsbertus Goos, Delft (NL); Raffaele Lorenzo Dellaca, Valmorea (IT); Ilaria Milesi, Sesto San Giovanni-Milan (IT)

(73) Assignees: Spatium Medical B.V., Rotterdam (NL); Politecnico di Milano, Milan (IT)

( * ) Notice: Subject to any disclaimer, the term of this patent is extended or adjusted under 35 U.S.C. 154(b) by 728 days.

(21) Appl. No.: 17/299,591

(22) PCT Filed: Dec. 2, 2019

(86) PCT No.: PCT/NL2019/050798
§ 371 (c)(1),
(2) Date: Jun. 3, 2021

(87) PCT Pub. No.: WO2020/117051
PCT Pub. Date: Jun. 11, 2020

(65) Prior Publication Data
US 2022/0054772 A1      Feb. 24, 2022

(30) Foreign Application Priority Data
Dec. 3, 2018    (NL) ...................................... 2022127

(51) Int. Cl.
*A61M 13/00*          (2006.01)

(52) U.S. Cl.
CPC ...................... *A61M 13/003* (2013.01); *A61M 2205/3327* (2013.01); *A61M 2205/3334* (2013.01); *A61M 2205/3344* (2013.01); *A61M 2230/42* (2013.01)

(58) Field of Classification Search
CPC ................ A61M 13/00; A61M 13/003; A61M 13/006; A61M 2205/3334;
(Continued)

(56) References Cited

U.S. PATENT DOCUMENTS

| 5,423,741 | A |   | 6/1995 | Frank | |
| 5,439,441 | A | * | 8/1995 | Grimsley | ............ A61M 13/003 600/561 |

(Continued)

FOREIGN PATENT DOCUMENTS

WO      WO 2017/014623 A1      1/2017

OTHER PUBLICATIONS

Malbrain et al., The role of abdominal compliance, the neglected parameter in critically ill patients—a consensus review of 16, Anaesthesiology Intensive Therapy, 2014, vol. 46, No. 5, 392-405, ISSN 1642-5758, DOI: 10.5603/AIT.2014.0062 (Year: 2014).*
(Continued)

*Primary Examiner* — Michael J Tsai
*Assistant Examiner* — Forrest B Dipert
(74) *Attorney, Agent, or Firm* — Leydig, Voit & Mayer, Ltd.

(57) ABSTRACT

An insufflator for exposing structures within an internal cavity forming a confined volume within an animal or human body, the apparatus including: an input conduit for exchanging gas with the confined volume; a gas insufflator for insufflation of gas into the confined volume through the input conduit, wherein the gas insufflator is configured to deliver an insufflator pressure to the confined volume, wherein the gas insufflator is configured to (super)impose at least one pressure or flow oscillation to obtain a forced
(Continued)

oscillating pressure or flow delivered to the confined volume, the forced oscillating pressure or flow having at least one component with a frequency and an amplitude; a monitoring unit for monitoring a response of the internal cavity to the forced oscillating pressure or flow for determining one or more physical properties of the internal cavity; and an adapter unit for adjusting the insufflation pressure based on the determined one or more physical properties of the internal cavity.

20 Claims, 15 Drawing Sheets

(58) Field of Classification Search
CPC ...... A61M 2205/3344; A61M 2230/46; A61M 1/85; A61M 2005/006; A61M 2205/3327; A61M 2230/42; A61M 5/142; A61M 5/172; A61M 5/1723; A61M 2005/1726; A61M 2025/0001; A61M 2025/0002; A61M 2025/0003; A61M 31/00; A61M 2202/02; A61M 2202/0225; A61M 2205/33; A61M 2205/3331; A61M 2205/50; A61B 17/3474
See application file for complete search history.

(56) References Cited

U.S. PATENT DOCUMENTS

| 2010/0147305 A1* | 6/2010 | Dellaca' | A61B 5/085 |
| | | | 600/533 |
| 2011/0030678 A1 | 2/2011 | Power et al. | |
| 2012/0266882 A1* | 10/2012 | Dellaca | A61M 16/0006 |
| | | | 128/204.23 |
| 2013/0150747 A1* | 6/2013 | Pompilio | A61B 5/085 |
| | | | 600/533 |
| 2015/0290387 A1* | 10/2015 | Möllstam | A61M 3/0201 |
| | | | 604/24 |
| 2018/0185062 A1 | 7/2018 | Geisz et al. | |
| 2019/0298947 A1* | 10/2019 | Trivikram | A61H 9/0078 |
| 2023/0177882 A1* | 6/2023 | Oldfield | A61B 5/087 |
| | | | 382/103 |

OTHER PUBLICATIONS

European Patent Office, International Search Report in corresponding International Application No. PCT/NL2019/050798, dated Feb. 10, 2020 (2 pages).

* cited by examiner

INSUFFLATOR FOR EXPOSING STRUCTURES WITHIN AN INTERNAL BODY CAVITY

CROSS-REFERENCE TO RELATED APPLICATIONS

This patent application is a U.S. National Phase of PCT International Application No. PCT/NL2019/050798, filed Dec. 2, 2019, which claims priority to Netherlands Application No. 2022127, filed Dec. 3, 2018, which are both expressly incorporated by reference in their entireties, including any references contained therein.

FIELD OF THE INVENTION

The invention relates to an apparatus for exposing structures within an internal cavity of an animal or human body for diagnostic and/or therapeutic endoscopic procedure. Further, the invention relates to a method of controlling an apparatus for exposing structures within an internal cavity of an animal/human body for a diagnostic and/or therapeutic endoscopic procedure.

BACKGROUND TO THE INVENTION

An insufflation apparatus is used for exposing structures within a cavity of an animal/human body, by insufflating gas into that body cavity, in order to obtain a field of vision, through the endoscope, to perform a diagnostic and/or therapeutic endoscopic procedure to one or more of the structures in the body cavity.

The insufflation apparatus can be used in minimal access surgery, allowing surgery through a few small incisions by introduction of a camera and instruments in the internal body cavity. The body cavity can be pressurized and workspace can be created such that the surgeon has sufficient room to operate inside the body. Endoscopy employs a small diameter instrument allowing to look within the body. In the thorax and abdomen a surgical field can be created for exploring the body cavity, by the insufflation of a suitable gas such as carbon dioxide gas to a desired pressure level.

Manual insufflation of gas into the internal cavity can make the surgical workspace quite difficult to maintain. Automatic insufflators maintain an intra-abdominal pressure at a set value, automatically limiting the flow when a desired pressure is reached. Also the insufflated volume of gas can be registered.

A volume of gas is insufflated into the thoracic or abdominal cavity to create workspace to allow surgery. However, the response of the cavity depends on the subject. Typically, current insufflators insufflate gas up to a preset pressure. The greater the insufflation pressure, the larger the volume of the body cavity created for carrying out the surgical procedure, yet greater is also the mechanical stress applied to the tissues surrounding the cavity. The gas pressure is typically maintained by measuring it at a relatively low frequency, typically 1 Hz or lower. Therefore, current insufflators have only limited feedback from their actions and change the applied insufflation gas pressure at a relatively slow frequency (approximately 1 Hz) to match the set pressure.

The pressure settings applied in clinical procedures are part of common practice and are applied for every patient (with some different settings used in children of different sizes) independent of body type and patient's conditions. Limited changes to the insufflation pressure are made when the achieved gas volume does not provide sufficient view or space to perform a procedure in. Applying generalized standard pressure settings often leads to either too little or too much pressure being applied to the tissues surrounding the cavity. While the first is easily overcome by increasing the applied pressure, the consequences of applying too much pressure are clinically significant and relevant. For example, in abdominal surgery the gas pressure needed for performing minimally invasive surgery creates upward pressure on the diaphragm, hampering ventilation. In patients that are difficult to ventilate (e.g. young children and the obese) the unnecessary application of too much insufflation pressure therefore hampers the ability to ventilate the patient properly.

Improving insufflation of internal confined body cavities may increase the percentage of procedures that can be performed using minimally invasive techniques. There is a need for improving the ability to perform minimal access procedures using an insufflator exerting less stress and possible harm to the intestines of the patient. It is desired to obtain an insufflator device which can insufflate the internal body cavity with improved safety.

SUMMARY OF THE INVENTION

It is an object of the invention to provide for an apparatus, a method and a system that obviates at least one of the above mentioned drawbacks.

Additionally or alternatively, it is an object of the invention to reduce the risk of exerting excessive stress to the body by insufflation.

Additionally or alternatively, it is an object of the invention to enable a better choice of the gas pressure set point within the internal cavity during insufflation.

Additionally or alternatively, an aim is to provide a quantitative assessment of the mechanical conditions of the tissues for the optimal and individualized titration of the insufflation pressure.

Thereto, the invention provides for an apparatus for exposing structures within an internal cavity of an animal or human body for diagnostic and/or therapeutic endoscopic procedure, the internal cavity forming a confined volume within the animal or human body able to provide information on the mechanical stress applied to the tissues surrounding the cavity, the apparatus comprising: an input conduit for exchanging gas with the confined volume, a gas insufflator for insufflation of gas into the confined volume through the input conduit, wherein the gas insufflator is configured to deliver an insufflator pressure to the confined volume, wherein the gas insufflator is configured to impose or superimpose at least one pressure or flow oscillation to obtain a forced oscillating pressure or flow delivered to the confined volume, the forced oscillating pressure or flow having at least one component with a frequency and an amplitude, a monitoring unit for monitoring a response of the internal cavity to the forced oscillating pressure or flow for determining one or more physical properties of the internal cavity, and an adapter unit for keeping the insufflation pressure below a threshold based on the determined one or more physical properties of the internal cavity.

On the basis of the one or more determined physical properties of the internal cavity, an optimal pressure setting for the insufflator apparatus can be determined. Advantageously, it can be determined or at least estimated how the increased pressure will affect the change of volume, and whether this pressure increase is still effective in increasing the cavity (with advantages for the surgeon in performing the surgery) or is mostly resulting in excessive stress to the

---

--- tissues (resulting in problems for patient recovery). The apparatus can induce a forced oscillating pressure/flow excitation to the insufflated confined volume formed by the internal body cavity, in order to derive mechanical properties of the internal body cavity. In this way, an appropriate pressure setting may be employed while reducing the risk of creating damage to the body. When the cavity is insufflated, the tissues and internal organs involved are stretched and/or compressed, changing their elastic properties. Therefore, by measuring the elastic properties of the cavity it is possible to indirectly assess the mechanical status of the tissues.

To create a working and a viewing space, the cavity where surgery takes place can be insufflated with carbon dioxide gas. The gas insufflator can be arranged for insufflating at a (preset) pressure or flow rate. The insufflated gas may for example be $CO_2$ gas. Other gases may also be used. Insufflation of gas into the body cavity other than the lungs can be achieved by applying a set gas pressure to insufflate gas into a body cavity. This can be done using a set gas flow. Insufflation of a gas volume increases the volume of the confined volume of the body cavity and creates the working/viewing space in which procedures can be performed. The input conduit is configured to provide an access to the confined volume enclosed by the internal cavity of the animal/human body.

Any body cavity has a tissue compliance that can be defined for every specific insufflation pressure. The workspace impedance/compliance can be a global parameter describing the combined effect of individual tissues. A compliance curve can be created by measuring pressure and volume during gas insufflation (with or without muscle activity or ventilatory support), with a linear part to the curve when lower pressures are applied, followed by a nonlinear part of the curve when higher pressures are applied. Overdistension of the body cavity by applying a relatively high insufflation pressure may cause a mechanical strain on the tissues. As a consequence, in this nonlinear part of the compliance curve less volume is gained per incremental increase in pressure when compared to the linear part of the compliance curve.

The mechanical response to the forced oscillations overimposed to the continuous insufflation pressure can be used for testing/determining mechanical characteristics of the internal cavity, based on which an input parameter for the insufflation is chosen (e.g. pressure or flow).

The mechanical properties of the tissues surrounding the cavity can be assessed from the response of the body cavity to the application of a (small) amplitude change in insufflation pressure, such response being measured either in terms of the resulting insufflation flow or as rate of displacement of the body surface in proximity of the cavity. This enables the calculation of several parameters representing the mechanical condition of the internal cavity including, for instance, the tissue impedance, which is an indicator of several mechanical properties, including the elastic properties of the surrounding tissues. Based on this determination, the insufflation can be selected and/or adjusted for optimization. Advantageously, the insufflation apparatus can identify a patient-tailored insufflation pressure able to minimize stress to tissues and/or reduce the effects on cardiorespiratory functions during endoscopy and/or endoscopic surgery.

Body size, weight and mean intra-abdominal pressure are not the only factors affecting the impedance. Other factors could be muscle activity, ventilation settings, perfusion, surgical manipulation.

Optionally, instead of oscillations of one or more frequencies, a forced impulse response can be used as forcing signal to probe mechanical conditions of the internal cavity. The characteristic of the impulse response of the cavity can then be measured by means of the monitoring unit. Such pressure impulse may be provided by flow control of the insufflator, or by a mechanical/acoustical pressure pulses. The measured impulse characteristic can be measured by pressure, flow or mechanical (acceleration) measurement.

Thanks to the knowledge of the mechanical properties of the cavity the operation of the insufflator can thus be improved, providing more benign conditions for the patient. In addition, a problem with the insufflation of $CO_2$ gas is the uptake into the bloodstream. Reducing the applied $CO_2$ pressure is therefore also of importance to reduce the uptake of $CO_2$ into the blood, reducing the harmful effects of $CO_2$ which causes acidosis and metabolic problems.

Advantageously, the surgical workspace can be better stabilized and the ventilation pressures that are required may be decreased. This may for instance be carried out even during a medical procedure, such as a surgery in a (body) cavity, e.g. for laparoscopic surgery.

The oscillations may be substantially sinusoidal oscillations at one or more frequencies.

The gas insufflator may be arranged to superimpose at least one pressure or flow oscillation to obtain a forced oscillating pressure or flow delivered to the confined volume, wherein the superimposed at least one pressure or flow oscillation is obtained by adding a pressure onto a preset pressure provided by the insufflator.

Optionally, the adapter unit is configured to keep the insufflation pressure or flow below a threshold.

Optionally, the monitoring unit is configured to determine the threshold based on the determined one or more physical properties of the internal cavity.

Optionally, the adapter unit is configured to keep the insufflation pressure or flow below threshold.

The insufflator pressure or flow may be an input parameter for obtaining a degree of insufflation. By keeping the insufflation pressure or flow below the threshold, a medical procedure may be carried out under safer insufflation conditions.

The apparatus may be employed for evaluating the mechanical response of the internal cavity to the forced pressure and/or flow insufflation oscillation applied via the input conduit of the insufflator. For this purpose, a forced oscillation signal can be applied for determining the impedance (cf. combination of resistance and reactance) and/or the compliance, for example. Determining or estimating the impedance may not be measured directly. The reactance can be derived from the compliance and inertance of the system.

Optionally, the monitoring unit is configured to determine the threshold based on the determined one or more physical properties of the internal cavity.

The apparatus can match an insufflator pressure setting of the gas insufflator with an optimal set point of the mechanical stress properties of the cavity. The apparatus can be configured to derive a set pressure where the elastic (impedance) behaviour of the internal cavity changes according to a preset threshold. In this way, an optimal set point can be identified, at which a volume is created without creating excessive stress, and an operator (e.g. surgeon) can choose, at what level he/she wishes to exert pressure, based on this optimal set point. Optionally, the gas insufflator can be actively controlled for the optimal set point, without having to manually set a pressure level of the insufflator.

The apparatus may include a pressure/flow manipulator near the internal cavity (e.g. in a trocar).

Different frequency ranges can be used as a forced oscillation frequency for providing information on tissue stress of the internal cavity of the body.

Optionally, the forced oscillating pressure includes a plurality of (preset) frequency components.

Advantageously, applying multiple frequencies at the same time (multiple sine waves) potentially allows identification of the impedance of different components of the body cavity and its contents, as well as quantification of the applied gas volume. The plurality of frequencies can be applied over-imposed to one another. It is also possible to apply the frequencies one at a time successively.

Optionally, the insufflator further includes a pressure sensor coupled to the input conduit for measuring the forced oscillating pressure within the confined volume and/or a flow sensor coupled to the input conduit for measuring the insufflator gas flow to the confined volume, wherein the monitoring unit is configured to determine the response of the internal cavity by measuring at least one of the insufflator gas pressure and gas flow during application of forced oscillating gas pressure.

Optionally, a differential pressure transducer is used for measuring the pressure and/or flow.

Optionally, the gas insufflator includes or is coupled to a turbine pump for generating the at least one pressure or flow oscillation to obtain a forced oscillating pressure or flow delivered to the confined volume.

Optionally, the gas insufflator includes or is coupled to a pressure generator for propagating the forced oscillating pressure inside the input conduit, wherein the pressure generator is a turbine pump.

Additionally or alternatively, an electro-acoustical transducer may also be used. For instance, a loudspeaker or similar voice-coil actuators may be used for generating the pressure perturbations. A set of other possible solutions based on bias flow in combination with voice coil valves may also be employed. It may be possible to employ piston pumps, for example.

The use of a turbine or pump for the creating of the forced pressure or flow oscillations may be beneficial with respect to other types of pressure generators such as a loudspeaker. A turbine-based arrangement can overcome several possible limitations intrinsic to loudspeakers systems, such as a limited frequency response at low frequencies, the need for large and cumbersome devices, and increased complexity of the device. A blower may provide a higher admittance in case of a pressure peak originating from or conducted by the insufflated body cavity.

Optionally, AC and DC insufflation pressures are generated separately. A manifold can be arranged for combining both signals and convey them through the insufflator tube to the input conduit (cf. trocar). Near or at the input conduit both flow and pressure can be measured. The flow probe can behave like a resistance. The rest of the system may represent the surgical workspace behavior. All pressures are relative to the pressure in the atmosphere.

Optionally, the apparatus includes a pressure generator for generating the oscillating insufflator pressure. The pressure generator may be a single generator arranged for providing the DC and AC component of the insufflator pressure. The pressure generator may thus integrate the generation of the mean pressure and forced oscillation pressure.

Optionally, the flow sensor is configured to have a substantially constant impedance behavior in a frequency range used for the forced oscillation. In this way the analysis of the data can be significantly simplified.

Optionally, means for assessing displacements at the body surface are employed for estimating elastic properties of tissues. The means for assessing displacement at the body surface may for instance include accelerometers. In an example, micro electro mechanical system (MEMS) accelerometers are used. Additionally or alternatively, other means may also be employed, such as for instance laser-based solutions for determining a displacement, velocity, and/or acceleration of a body surface near the body cavity. In a different example, the body undergoes abdominal insufflation (e.g. of $CO_2$ gas), in which the insufflated gas volume is measured using CT scanning.

Optionally, at least one preset component has a frequency different from a lung ventilation frequency imposed by a ventilation means arranged for delivering a therapeutic respiratory pressure to the respiratory system of the animal/human body.

The apparatus may be configured to perform forced oscillations for abdominal endoscopy for determining an optimal pressure setting for obtaining improved surgical workspace, while optionally taking into account ventilation parameters, i.e. mechanical ventilation of the subject using a ventilator or breathing device.

Additionally or alternatively, the pressure and/or flow at the input conduit is monitored, while mechanically ventilating the patient, wherein the imposed pressure or flow to the lungs by means of the mechanical ventilator includes one or more oscillations used for determining some of the properties of the confined volume. In this way, the forced oscillations can be provided by means of the mechanical ventilation. In an example, the forced oscillations are exclusively provided by means of the mechanical ventilation of the lungs.

Optionally, the monitoring unit is configured to determine one or more physical properties of the internal cavity on a periodic basis for monitoring changes in one or more physical properties of the internal cavity, and wherein the adapter unit is configured to dynamically adjust the insufflation pressure or flow based on changes in the one or more physical properties of the internal cavity.

Advantageously, the gas insufflator can be controlled according to a pressure set level determined by forced oscillations. The insufflation can be dynamically controlled using determined information about the internal body cavity. Frequencies up to 10 Hz expose visco-elastic behavior of the surgical workspace. The peak to peak amplitude will be large enough such that the signal is distinguishable from the noise and distortions. Large peak to peak amplitudes would result in non-linear biomechanical behavior of insufflated body cavity and complicate estimation of impedance. Therefore the amplitude should be kept as low as possible.

At lower the frequencies the visco-elasticity of tissues dominates the overall mechanical properties. Frequencies lower than 1-2 Hz are therefore in general more sensitive to the visco-elastic behavior of the surgical workspace due to the body tissues. The response of the system will include also the mechanical behavior of the conduit system (mainly describable as resistance and inertance). Nevertheless, the changes in the mechanical properties of the conduit could be considered as negligible compared to the ones of the tissues. Frequencies higher than 15-20 Hz can be used to determine the capacitance/volume of the surgical workspace being less sensitive to the tissue response.

Optionally, the insufflator is arranged to generate at or near the input conduit a variable pressure with a peak to peak amplitude possibly lower than 10 cmH$_2$O, preferably lower than 5 cmH$_2$0 and, in a more preferably setting, at approximately 2 cmH$_2$O and with a frequency range of 0.1-100 Hz. Optionally, the forced oscillating pressure or flow can include a plurality of (preset) frequency components. The physical properties of the internal cavity may be determined in an improved way by operating the apparatus within these parameters. It will be appreciated that other ranges may also be employed.

Optionally, the excitation unit is configured to perform a sweep of the frequency of the forced oscillating pressure while the continuous pressure is provided.

Optionally, the excitation unit is configured to perform a mean distending pressure sweep during the application of the oscillating pressure.

Optionally, the excitation unit is configured to perform a frequency sweep of the forced oscillating pressure.

Optionally, the one or more physical properties of the internal cavity are estimated by means of model fitting.

An insufflation pressure may be selected by using a constant phase model to fit impedance data for identifying more specific parameters to identify an optimal insufflator pressure to be applied for the patient. A bias flow manipulation arrangement based on a pressure/flow manipulator near the cavity (e.g. within a trocar) may be used. Optionally, the one or more physical properties of the internal cavity include at least one of: a mechanical impedance, expressed as a mechanical resistance and mechanical reactance, or a compliance, an elastance or a tissue damping of the internal cavity. The frequency response of a system is commonly reported in terms of multiple parameters, usually either modulus and phase or real and imaginary part. When the frequency response is computed considering flow (input) and pressure (output) at the inlet of the system and a simple resistance-inertance-compliance model is considered, the real part represents the resistance of the system and the imaginary part the reactance. By using more specific mathematical models it is possible to estimate parameters typical of the mechanical behavior of biological tissues, for example the use of a constant-phase model provides the possibility to estimate tissue damping, elasticity and hysteresivity. Even if all these variables are estimated from the same measured data, they report differently the contribution of the several physical phenomena determining the overall mechanical properties and, therefore, can be conveniently used for specific analysis. For example, change of resistance over time at low frequencies is expected because it is markedly affected by visco-elastic effects. Conversely, at high frequencies the resistance is mostly related to Newtonian resistance and, therefore, it can be used to identify occlusion in the conduit system towards the patient. Also, the reactance at high frequencies can be monitored to detect changes in workspace gas volume. Information about resistance at several frequencies can be combined to reactance to expose specific visco-elastic model parameters, such as tissue elastance and tissue damping related to the tissues surrounding the surgical workspace. Other mechanical or acoustical properties may also be derived.

Optionally, the gas insufflator includes a trocar as input mechanism arranged for being sealingly inserted into the internal cavity of the animal or human body.

The invention allows measuring the mechanical conditions of the insufflated cavity and its contents and how they change with insufflation pressure to allow identifying the range of optimal pressures that avoids over-distending the abdominal tissues and/or minimize hemodynamic and respiratory impairments. This may be obtained in real-time even during surgery in order to track changes in a patient's condition, for example when ventilator parameters are adjusted, allowing a continuous optimization of the insufflation pressure.

According to an aspect, the invention provides for a surgical system including the apparatus according to the invention.

The forced oscillation needed to probe the mechanical properties of the cavity can be applied by means of the insufflator of the apparatus for the optimization of the applied insufflator pressure and acquired space in endoscopy and endoscopic surgery, i.e. space obtained by the insufflated confined volume. For example, a predetermined pressure wave may be applied to the confined volume of the internal cavity of a subject through the input conduit overimposed onto the continuously delivered pressure. Analysis of flow resulting from the applied non-continuous pressure component/components allows determination of the tissue mechanical properties of the internal cavity, with which an estimation of tissue stretch can be found. By employing this approach in endoscopy and endoscopic surgery, the applied gas insufflation pressure can be optimized by measuring one or more physical properties of the internal cavity, such as for example a tissue reactance.

The apparatus may include a turbine arrangement with means of pressure and/or flow measurements with which an insufflated pressure could be applied to the abdomen and in addition predetermined pressure perturbations. During an insufflation pressure step several perturbation frequencies can be applied simultaneously and/or successively.

According to an aspect, the invention provides for a computer-controlled method of operating an insufflator intended to expose structures within a cavity of the animal or human body for a diagnostic and/or therapeutic endoscopic procedure. The method may be carried out by means of a controller.

The apparatus and method may be employed in several types of endoscopy and endoscopic surgery procedures, for example in abdominal (both preperitoneal, intraperitoneal and retroperitoneal) and thoracic surgery, as well as in procedures in which the intestines are insufflated with gas for visualization (e.g. a colonoscopy).

The insufflator according to the invention can be used for monitoring and/or optimization. It will be appreciated that the term 'exposing structures' may relate to determining and/or revealing properties of an internal cavity in a human or animal body.

It will be appreciated that any of the aspects, features and options described in view of the method apply equally to the apparatus, method and the described system. It will also be clear that any one or more of the above aspects, features and options can be combined.

BRIEF DESCRIPTION OF THE DRAWING

The invention will further be elucidated on the basis of exemplary embodiments which are represented in a drawing. The exemplary embodiments are given by way of non-limitative illustration. It is noted that the figures are only schematic representations of embodiments of the invention that are given by way of non-limiting example.

In the drawing.

DETAILED DESCRIPTION

Figure 1:
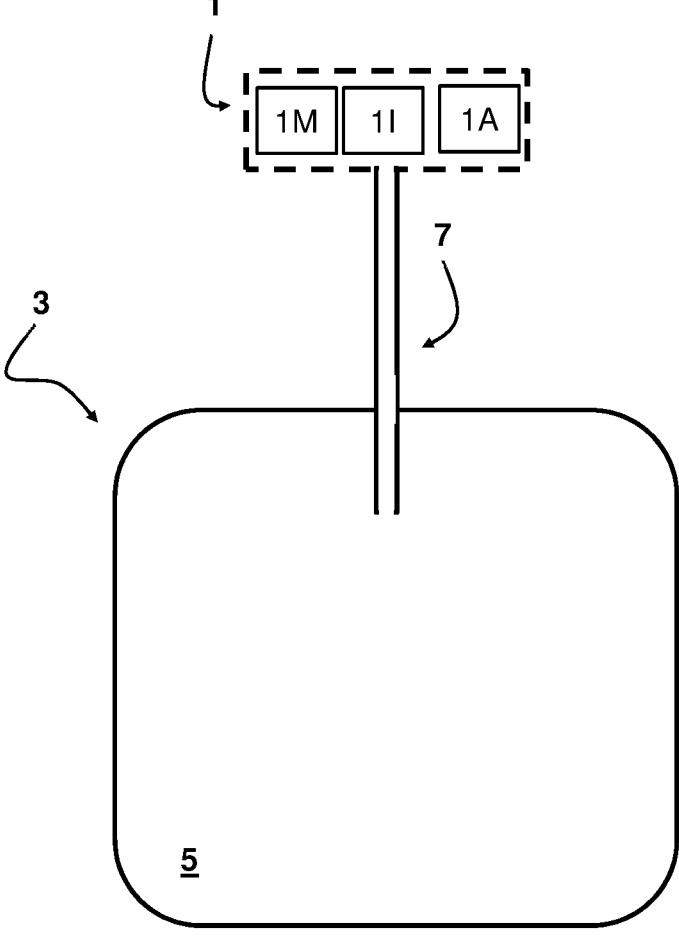
FIG. 1 shows a schematic diagram of an internal cavity insufflated by pressurized insufflation gas through an input conduit of an insufflator.

FIG. 1 shows a schematic diagram of an apparatus 1 used for insufflation of an internal cavity 3. The apparatus 1 is arranged for exposing structures (e.g. organs) within the internal cavity 3 of a human body for diagnostic and/or therapeutic endoscopic procedure. The internal cavity 3 forms a confined volume 5 within the human body. The apparatus 1 comprises an input conduit 7 for exchanging gas with the confined volume 5. The apparatus 1 further comprises a gas insufflator 1I for insufflation of gas into the confined volume through the input conduit, wherein the gas insufflator 1I is configured to deliver a pressure to the confined volume 5, wherein the gas insufflator is configured to impose at least one pressure or flow oscillation to obtain a forced oscillating pressure or flow delivered to the confined volume, the forced oscillating pressure or flow having at least one preset component with a frequency and an amplitude. Through the input conduit 7, which can be brought in fluid communication with the confined volume 5 of the internal cavity, the pressurized insufflation gas can be provided in the confined volume 5. The apparatus 1 further includes a monitoring unit 1M for monitoring a response of the internal cavity 3 to the forced oscillating pressure or flow for determining one or more physical properties of the internal cavity 3. Further, the apparatus 1 includes an adapter unit 1A for adjusting the insufflation pressure or flow (in any combination) based on the determined one or more physical properties of the internal cavity 3.

The apparatus 1 can be used for optimizing the applied pressure in any endoscopic or surgical endoscopic procedure in which a gas is used for insufflation of a body cavity 3. A device for the application of the forced oscillations can be either part of a gas insufflator 1I or a separate device that adds an oscillating pressure (and/or flow) wave to a (DC) gas pressure provided by a separate device. Oscillations can be created by means of a turbine, membrane, piston, transducer, valve, etc. A turbine may provide an improved control over the pressure oscillations. The effects can be measured by high-frequency flow and pressure sensors, which can be located within the insufflator, for example at a separate device or at the inlet into the body cavity.

In an example, the apparatus is configured for measuring both the flow and the pressure supplied to the confined volume 5 of the internal cavity 3. The sampling frequency can be chosen sufficiently high for measuring the perturbation frequencies. Data obtained during measurements may be stored for real-time or later analysis.

Figure 2:
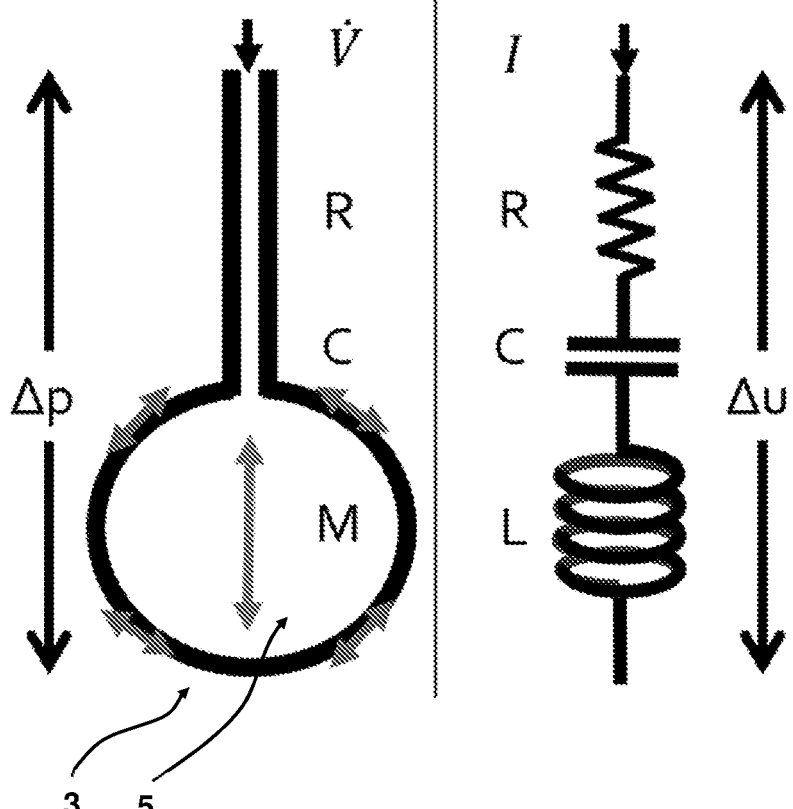
FIG. 2 shows a schematic pneumatic-electrical analogy for insufflation.

FIG. 2 shows a schematic pneumatic-electrical analogy for insufflation. The internal cavity 3 can be represented by an inflatable volume (cf. balloon model). The apparatus 1 shown in the exemplary embodiment of FIG. 1 can be used for providing pressurized insufflation gas to the internal cavity 3. The pneumatic circuit can be drawn as an electric one, wherein pressure P equals voltage U, flow equals current I, mechanical resistance R equals electrical resistance R, compliance C equals conductance C, and the mass M of the gas in the body cavity equals to the inductance L.

In minimal access surgery, the surgeon uses small incisions to enter the surgical site. Minimal access surgery has shown to be advantageous over conventional surgery because it reduces the chance of infection, amount of postoperative pain and results in less scar tissue. Within the body there is no physiological space within most body cavities for the surgery, yet space can be created by insufflating a pressurized gas. Typically, a pneumoperitoneum is created by insufflating carbon dioxide gas through a trocar into the surgical site. The surgical workspace is commonly defined as the volume of the pneumoperitoneum.

A large surgical workspace facilitates the surgeon and shortens the duration of surgical or diagnostic procedures. Shortening the procedure improves medical safety and reduces the amount of postoperative pain. This workspace can be enlarged by increasing the pressure with which the carbon dioxide gas is insufflated. Using high pressures for creating surgical workspace can have adverse effects. Firstly, additional carbon dioxide diffuses into the blood vessels surrounding the surgical workspace, imposing a load onto the respiratory system requires adjustment of the mechanical ventilator settings. Secondly, organ perfusion is reduced when subjected to high internal pressure levels. For example, partial or total lung collapse will occur when the mechanical ventilator settings are not adjusted accordingly. Thirdly, the tissues surrounding the surgical workspace get damaged due to overdistension.

The relation between the pressure used for insufflation and the created surgical workspace volume is described by a compliance curve. The surgical workspace compliance can be defined as $C_{ws}=\Delta V/\Delta p$, with $\Delta V$ being a change of a volume of the confined volume of the internal cavity and $\Delta p$ being a change of the imposed pressure within the confined volume. The surgical workspace gain per pressure increment is influenced by body size, tissue conditions (aging) and affected by muscle activity (neuromuscular blockade).

Tissue surrounding the surgical workspace stiffens when it is overdistended, reducing the surgical workspace compliance. If the surgeon can be informed about workspace compliance, he or she can make an adequate decision on the requirement of additional space, even when it will lead to overdistension of the tissue. The apparatus according to the invention can be configured to use a forced oscillation for identifying changes in surgical workspace compliance. This can be done continuously or non-continuously. The apparatus may be used for preventing overdistension of the surrounding tissues during insufflation. Optionally, the information on the surgical workspace compliance can be used by the apparatus for providing an automated control of insufflation.

The apparatus may include means for measuring or estimating the volume and pressure to determine the patient-specific compliance curve. Leakage of carbon dioxide may inhibit estimation of the created volume by integrating the volumetric flow rate. Therefore reliable volumetric measurements may be difficult to obtain without prolonging the surgical procedure. The lack of information on the volume of the surgical workspace deters continuous monitoring of surgical workspace compliance.

Mechanical impedance is defined as the amount of pressure needed to create flow, $Z(\omega)=p(\omega)/V(\omega)$. The surgical workspace impedance, $Z_{ws}$, can be determined by measuring the pressure and flow at the trocar:

$$Z_{ws}(\omega) = \frac{P_{trocar}(\omega)}{\dot{V}_{trocar}(\omega)}$$

A reduction in compliance can increase the impedance, more pressure is needed to create the same flow. The whole detection method can be based on the electrical analogy of a resistor (R), capacitance (C) and inductor (L) in series. Pressure would equal voltage and flow would equal current. In the pneumatic domain the $Z_{ws}$ can be modeled as a balloon being inflated, as depicted in FIG. 2 for clarification. Changes in the capacitive properties of the internal cavity would indicate a change in surgical workspace compliance.

The frequency behaviour of the input impedance $Z_{ws}$ can be decomposed into resistance, $R_{ws}$, and reactance, $X_{ws}$:

$$Z_{ws}(\omega)=R_{ws}(\omega)+i \cdot X_{ws}(\omega)$$

Reactance itself can also be decomposed, at low frequencies the capacitance will dominate the impedance behaviour:

$$X_{ws}(\omega) = \omega \cdot L - \frac{1}{\omega \cdot C}$$

At the resonance frequency the reactance can become zero, therefore the impedance behaviour can be dominated by the resistance. At higher frequencies the reactance can become more positive and the behaviour can be dominated by the inertial properties of the system.

Forced oscillations may be applied to input parameters (pressure, flow, etc.) of the insufflator for identifying changes in surgical workspace compliance. For instance, the frequency response may be used for monitoring the surgical workspace compliance for preventing overdistension of the surrounding tissues forming the internal cavity. Small forced pressure oscillations around a constant pressure can be used to determine the mechanical compliance of the internal cavity.

The apparatus 1 can be configured to provide automated control of the insufflation based on the compliance of the internal cavity forming the surgical workspace. Low frequency forced oscillations can be used to monitor surgical workspace compliance (cf. impedance model of a balloon).

Figure 3:
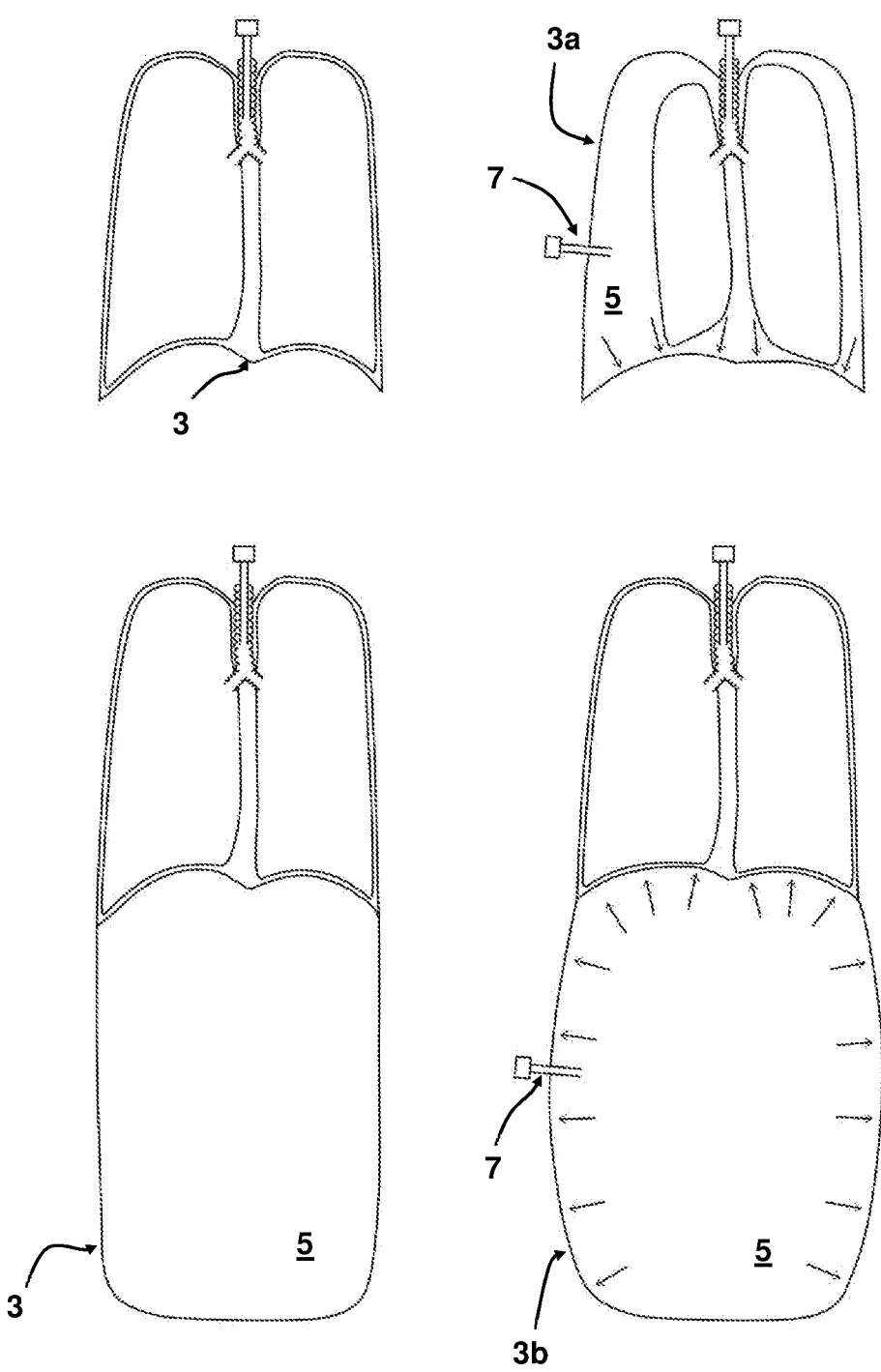
FIG. 3 shows a schematic diagram of a thoracic and abdominal cavity and the influence of insufflating a pressurized insufflation gas.

FIG. 3 shows a schematic diagram of a thoracic cavity 3a and abdominal cavity 3b of a human body and the influence of insufflating a pressurized insufflation gas. The behavior of the internal cavities 3a, 3b may be determined by the surrounding tissue forming the confined volume. The apparatus can include an insufflator configured to perform forced oscillations for determining oscillation mechanics of the internal cavity defining a surgical workspace. The insufflator of the apparatus can be in fluid communication with the confined volume of the internal cavity 3a, 3b through the input conduit 7. Based on the oscillation mechanics, physical properties of the internal cavity 3a, 3b can be determined, based on which the insufflator pressure can be selected. Hence, advantageously, a patient-dependent insufflator pressure can be obtained. It can be prevented that a too high internal pressure is applied for increasing the surgical workspace, such that damage to the surrounding tissue due to overdistension can be prevented while a large surgical workspace can be created which can facilitate the surgeon and shorten the duration of a (minimal access) surgical procedure.

Surgical workspace compliance describes the relation between the volumetric gain rate of surgical workspace and the pressure used. The use of the forced oscillations can enable monitoring of the surgical workspace compliance to prevent overdistension, without prolonging the surgical procedure. The apparatus and method can be used for applying endoscopic forced oscillations (e.g. in insufflation gas pressure) on the internal volume 5 of an animal or human body formed by the internal cavity 3. Optionally, frequency and pressure sweeps can be performed to investigate if this technique can be used to monitor surgical workspace compliance. Using 6 Hz forced pressure oscillations with a peak-to-peak amplitude of 2 hPa amplitude can be used to monitor changes in surgical workspace compliance. The apparatus is safe for the subjects and can be used to prevent overdistension and can enable closed-loop controlled insufflation of the surgical workspace.

In this example, the patient is also mechanically ventilated using a breathing device. It may be desired to determine the physical properties of the internal cavity automatically and accurately during mechanical ventilation of the patient. For humans ventilation frequencies may range from as low as approximately 0.3 Hz in adults to 1 Hz or even beyond in children. The apparatus 1 may be configured to adequately filter out the ventilation frequency, or for example choose perturbation frequencies based on patient properties (e.g. age, length, weight) that do not overlap with ventilation frequencies. The apparatus may be configured to receive the properties linked to the human body for determining the ventilation frequency. The insufflator of the apparatus may be provided with specific modes for neonates/children and adults (e.g. limiting the pressure and flow in children). These settings may be used to apply different frequency filters to filter out the ventilation.

The apparatus, notably, insufflator unit 1I may include a turbine (not shown). The apparatus may further include a closed-loop controller for controlling the turbine. A turbine may enhance the forced pressure signal quality in the dynamic range useful for this application (compared to loudspeakers, it can more efficiently provide high amplitude forcing signal also at low frequency), moreover, differently from voice coil valves or similar, it can modulate the cavity pressure without requiring releasing the inflation gas outside the cavity. The closed-loop controller can be configured for guaranteeing that the mean target pressure is reached.

The apparatus according to the invention can be used for endoscopy, laparoscopy, thoracoscopy, etc. The structure of the lungs is very different from the laparoscopic workspace. The surgical workspace formed by the internal cavity has other properties that require more complicated models than the lungs. Other organs, with their own impedance properties, reside within the surgical workspace. The workspace is surrounded by the abdominal wall, other organs and the diaphragm. Multiple frequency bands can be used to identify their contribution to the total impedance.

Advantageously, the relation between insufflator pressure and the created volume can be determined without requiring measurements using a CT-scanner. Forced oscillations can be applied onto the surgical workspace for determining changes in surgical workspace compliance without pro-longing the surgical procedure and protecting the subject/patient from harm, improving the medical safety.

Figure 4:
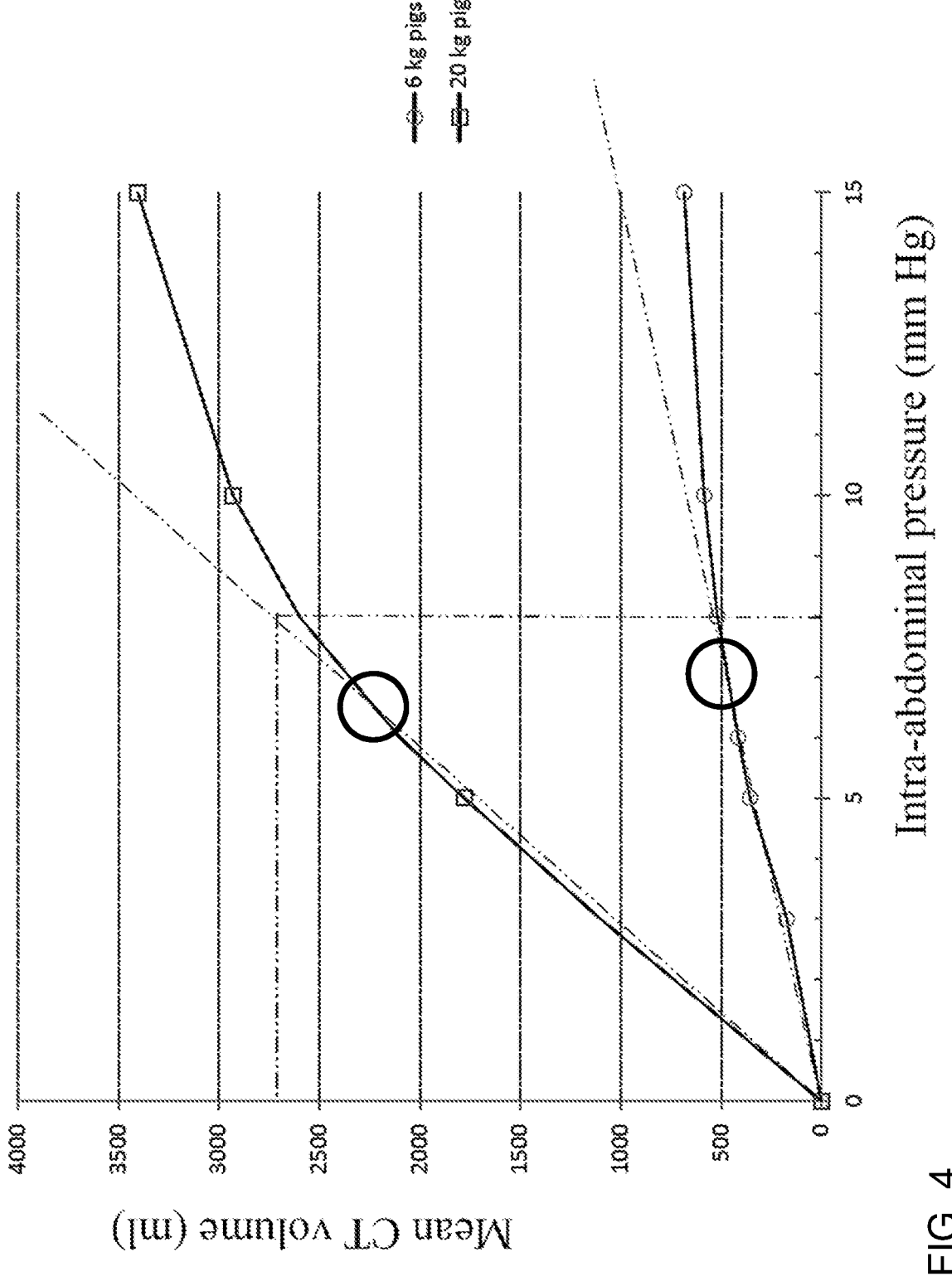
FIG. 4 shows a graph of intra-abdominal pressure versus volume for two subjects.

FIG. 4 shows a graph of intra-abdominal pressure versus volume for two subjects. By means of the apparatus 1 physical properties or mechanical conditions of the internal cavity 3 can be determined which can be utilized for selecting a threshold for the insufflator pressure. An index may be used to assess a threshold for the insufflation pressure. This index may be related to a change in the elasticity with a change of the insufflation pressure. When the tissues forming the internal cavity are relaxed, that is at a low insufflation pressure, a small variation of pressure is expected to produce a relatively large increase in the volume of the confined volume formed by the internal cavity. As the insufflation pressure is increased, the gain in volume per pressure increment can be reduced because the tissues have already been stressed to some extent. At low insufflation pressures the internal cavity may be more compliant but then as the pressure increases, the internal cavity may become increasingly stiffer because of the stretch of the tissues.

The elastic properties may be measured as the compliance, as the reactance of the internal cavity and/or as the pressure transmission. Alternatively, mathematical model specifically developed for describing the viscoelastic behaviour of biological tissues forming the internal cavity can be used. For instance, a constant phase model can be employed.

Once the elastic properties have been estimated, the compliance gain from one step to the next can be referred to the initial gain in the elastic properties that is expected to be the most significant. Then, at each step in insufflation pressure, the gain in the elastic properties compared to the initial one can be assessed to evaluate whether it is still worthwhile to increase the pressure in order to gain volume, or whether a next pressure increment will lead to a negligible gain in volume at the expense of potentially dangerous increase in insufflation pressure. By using this approach that compares the current compliance at a certain inflation pressure to the initial value, the pressure optimization can be performed online since no prediction on the next value of the elastic property is needed. A possible threshold on this index can be a variation of the 5-15%, for example 10%. Other values may also be employed.

Figure 5:
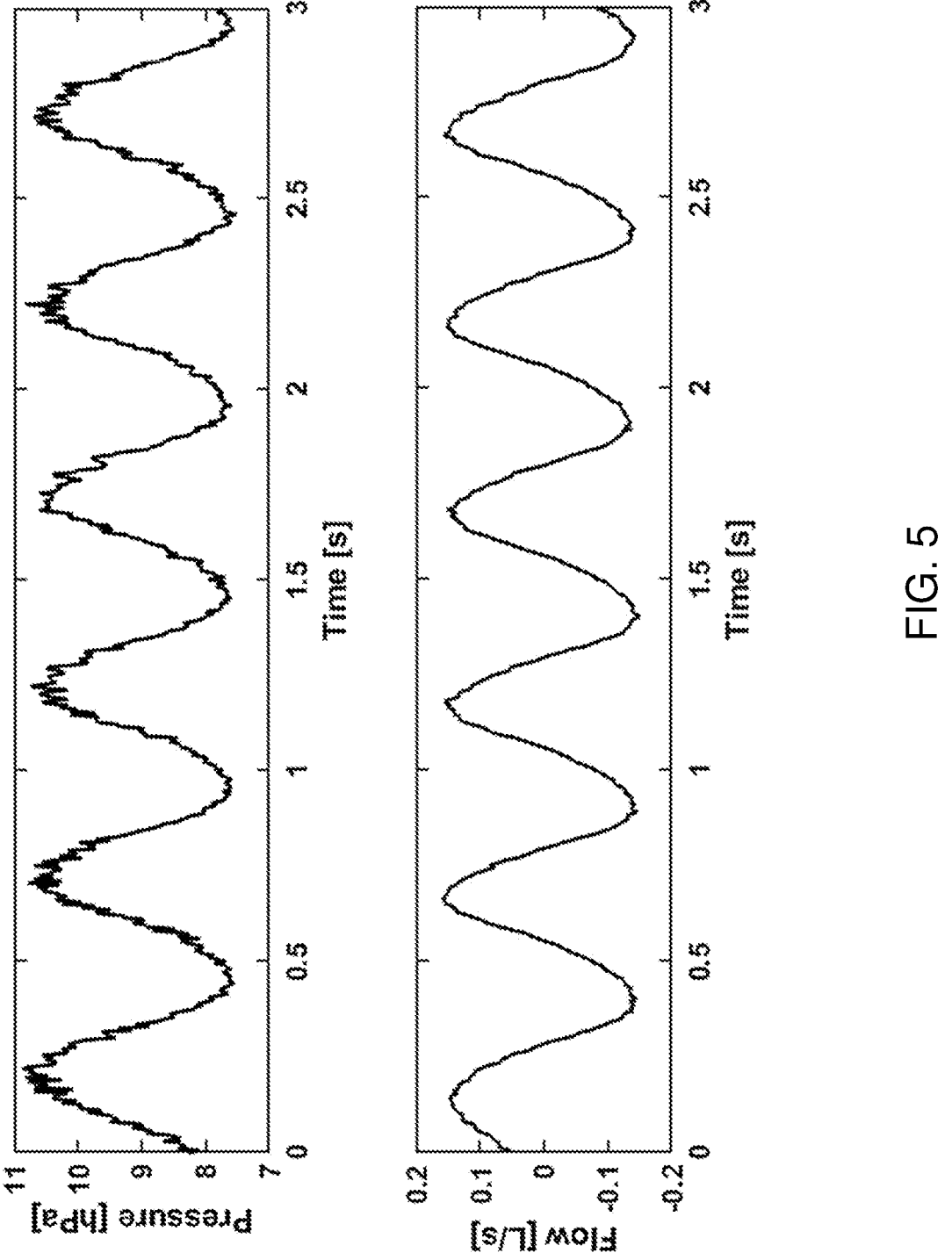
FIG. 5 shows graphs of oscillating pressure and flow versus time.

FIG. 5 shows graphs of oscillating pressure and flow versus time. An oscillating insufflation pressure may be applied to the confined volume 5 of the internal cavity 3 via the input conduit 7 of the insufflator of the apparatus 1. As a result, an oscillating flow is obtained. The oscillating pressure may for instance be generated using a turbine. The pressure and flow may be measured at or near the input conduit 7 for instance. The apparatus can be configured to determine one or more physical properties from the forced pressure oscillations and the flow response. The analysis may be performed in the frequency domain or the time domain.

Figure 6:
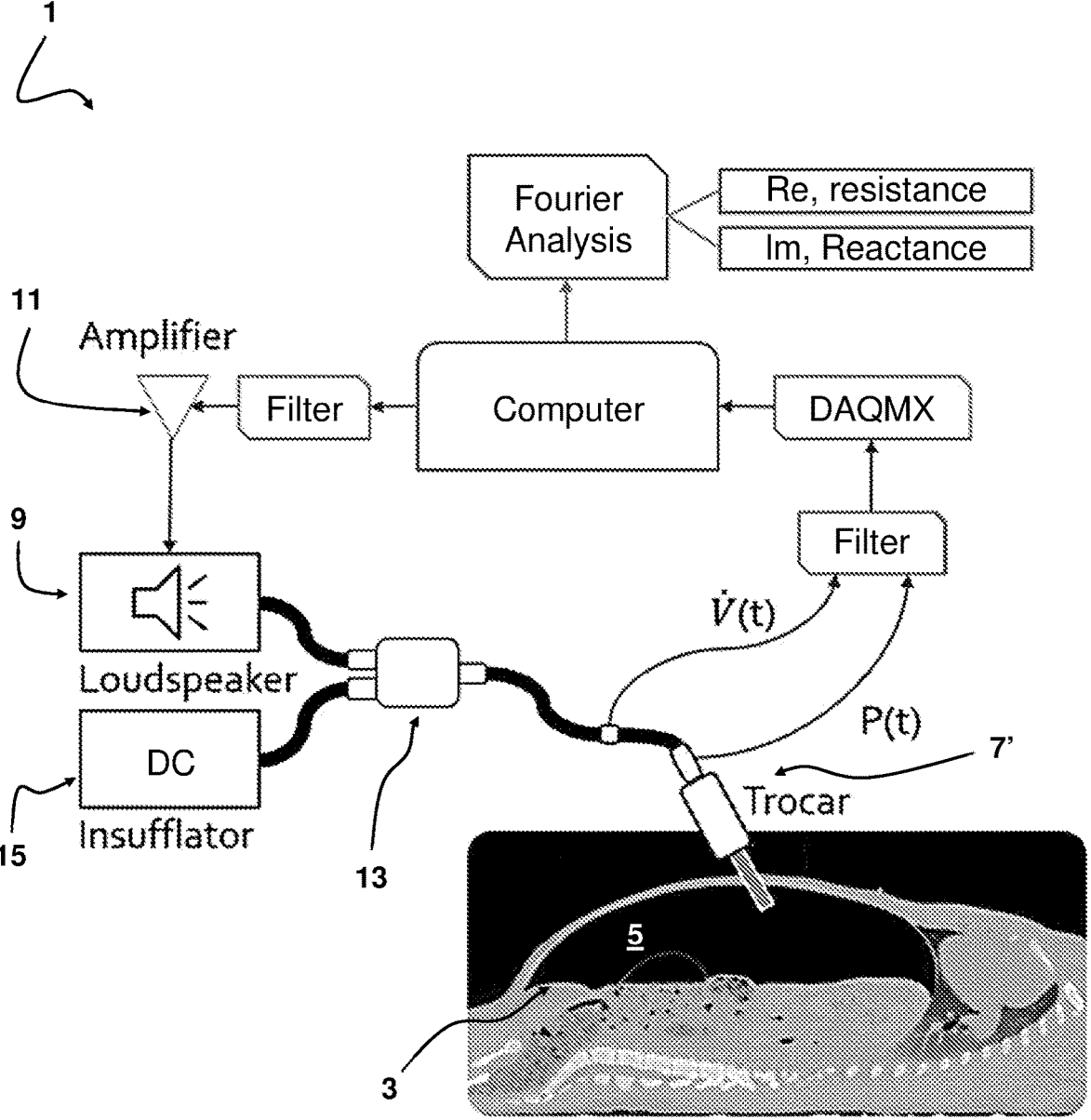
FIG. 6 shows a schematic diagram of an apparatus.

FIG. 6 shows a schematic diagram of an apparatus 1. The apparatus 1 is configured to perform endoscopic forced oscillations for surgical workspace impedance measurements. Insufflation gas may be provided to the confined volume 5 of the internal cavity 3 by means of a trocar 7'. The insufflation pressure ($p_{troc}$) and flow ($\dot{V}_{troc}$) can be measured close to the trocar 7'. The forced oscillations may be generated using an acoustic transducer, where acoustic has to be intended as transducer normally used in the acoustic frequency range, for instance, a speaker 9 and power amplifier 11 can be used for creating the forced pressure oscillations. The amplifier 11 may have a built-in low pass filter (e.g. with a 200 Hz cutoff frequency). A manifold 13 can be used to combine the pressure from a DC insufflator unit 15 with the forced pressure signal from the speaker 9. The manifold 13 can be connected to an insufflation tubing set with a gas filter. A pressure release valve may be connected to the manifold 13 for medical safety. Instead of generating pressure oscillations by acoustic transducer also a turbine may be used in an advantageous embodiment. The turbine may provide improved pressure/flow oscillations of preset and/or well defined amplitude and frequency, such that more accurate results can be obtained particularly at low frequencies where acoustic transducer are not suitable.

Information on oscillatory behaviour of the subject's internal cavity can be obtained through applying frequency sweeps. During these frequency sweeps, the mean applied insufflator pressure may be kept constant. The frequency sweep may for instance be executed stepwise. The response to every frequency between a frequency range (e.g. 4-20 Hz) may be recorded for a predetermined period of time.

Changes in surgical workspace impedance can be investigated by applying pressure sweeps. The mean insufflator pressure can be increased stepwise (e.g. from 1-20 hPa). At each pressure step the forced pressure signal, that are sequential oscillating pressure waves covering different frequencies, can be applied for a predetermined period of time. During these sweeps the forced pressure signal amplitude can be kept constant or slightly increased at low frequencies to improve the signal to noise ratio. Between every step sufficient time may be provided such that the insufflator can reach the mean target pressure and the viscous component of the tissues can reach the actual expansion associated at that distending pressure.

In an advantageous embodiment, the insufflation pressure is stepwise increased with each step hosting a frequency sweep.

During the frequency and pressure sweeps the trocar pressure ($p_{troc}$) and flow ($\dot{V}_{troc}$) can be measured at the input conduit 7, e.g. at a gas intake port of the trocar 7'. Additional pressure measurements may be performed at the manifold 13. In an example, a plurality of pressure transducers can be used. In an example, two transducers are used for differential flow pressure measurements in a fixed orifice flow sensor. To prevent aliasing the electrical signals can be filtered, for example using an analog low-pass filter. The signals may be low-pass filtered and re-sampled for storage and computational analysis.

In case a certain kind of flow sensor is used, for example an orifice flow sensor, the frequency response of the flow sensor can depend on the mean insufflator pressure and forced signal frequency employed therefore correction factors may be used to compensate. These correction factors can be calculated, for example, from measurements on a reference impedance, whose theoretical impedance can be determined. The analysis may for instance be carried out in the frequency domain, with resistance being the real part of the impedance and the reactance being the imaginary part of the impedance.

Optionally, the forced oscillation frequencies are chosen such that information on surgical workspace impedance and/or compliance can be obtained while avoiding detrimental interaction with the mechanical ventilation.

Figure 7:
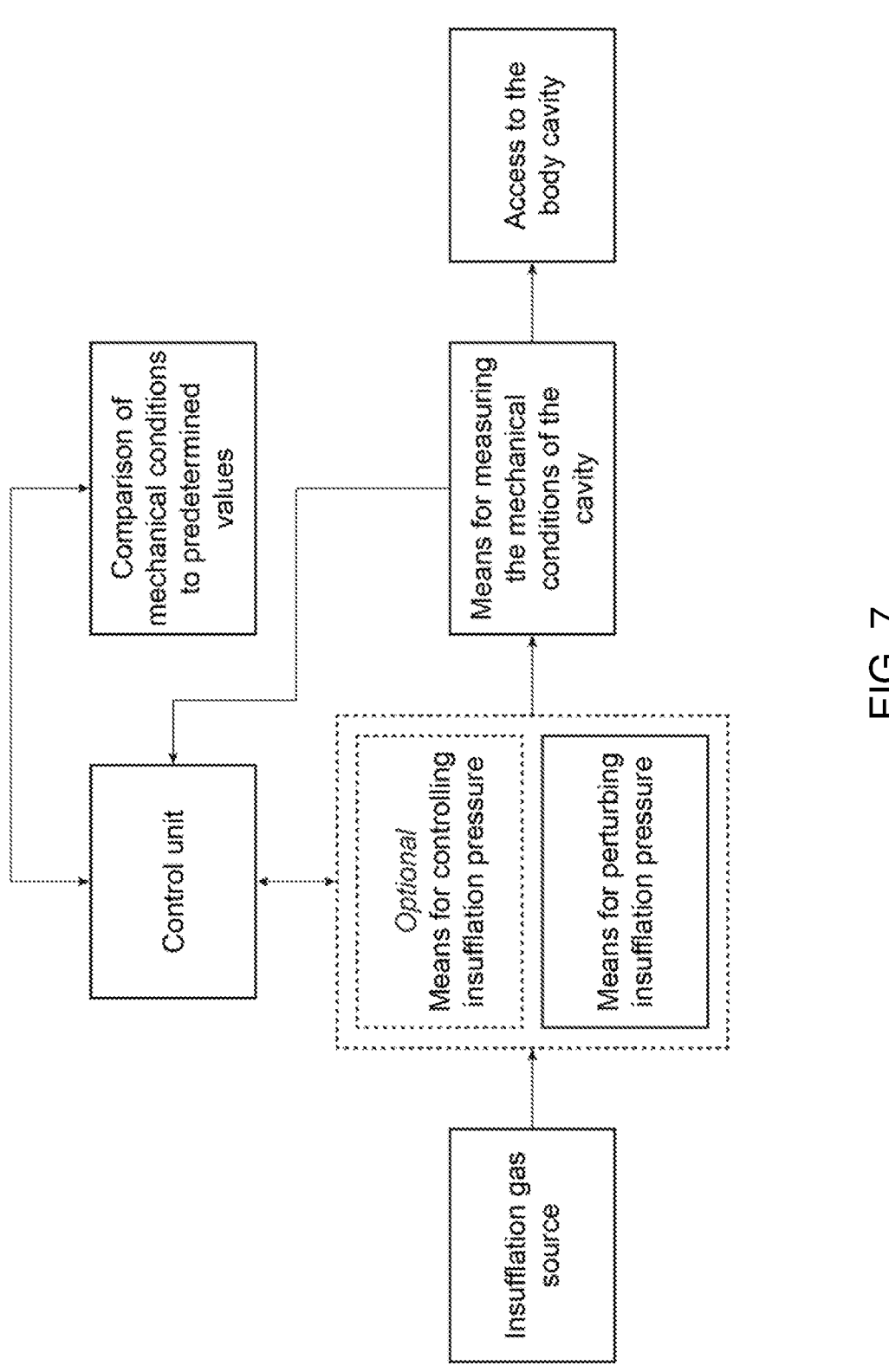
FIG. 7 shows a schematic block diagram of an apparatus.

FIG. 7 shows in more detail a schematic block diagram of an apparatus 1. The apparatus 1 is arranged for generating and provide an insufflation pressure of a gas (usually $CO_2$) to the internal cavity. To the insufflation pressure a pressure perturbation may be added for measuring the mechanical properties of the insufflated cavity, without increasing the level of invasiveness of the procedure. The insufflation pressure and/or the displacement of the cavity can be measured either by measuring the insufflation flow or the body surface displacement and using these measurements for estimation of the mechanical conditions of the system. Based on the mechanical conditions, a threshold can be provided for the titration of insufflation pressure. Advantageously, these steps may be carried out in real-time by the apparatus.

The apparatus may include a source of insufflation gas ($CO_2$ or any other gas that is used to create workspace); an arrangement for generating insufflation pressure; an arrangement for creating a pressure perturbation on the insufflation gas; means for measuring the mechanical conditions of the insufflated body cavity wall; an access to the internal cavity 3 through the body surface; and means for comparing the mechanical conditions of the body to predetermined values/thresholds for identifying the optimal insufflation pressure in real-time.

In an example, the apparatus is utilized for abdominal insufflation, wherein an optimal setting of the intraabdominal pressure (IAP) is determined. It will be appreciated that the apparatus may be used for insufflation of other internal body cavities 3 (with the exception of the lungs).

The access to the internal cavity 3 may be a standard trocar as it is, or a modified trocar with the addition of channels used to access the cavity and/or means to measure/manipulate the insufflation flow and/or pressure.

The insufflated internal cavity 3 can be characterized by means of its physical properties, such as its elasticity. Elastic properties of the internal cavity 3 can be quantified by means of mechanical compliance, mechanical reactance, and pressure wave transmission.

An easy way to assess compliance of the internal cavity 3 and coupled tissues is to provide a pressure step to the cavity and to measure the change in confined volume 5 due to that pressure step. In this case, compliance can be assessed as:

$$C = \frac{\Delta V}{\Delta P}$$

With C being the compliance of the internal cavity 3 defining the confined volume, $\Delta V$ being a volume change of the confined volume 5 and $\Delta P$ being a gas pressure change imposed on the confined volume 5.

Volume can be accurately measured by means of a computer tomography (CT) system or a magnetic resonance imaging (MRI) scanner, but both approaches may be difficult for use because of the long post-processing time needed to extract the volume from the images and the time and effort imaging would take for optimization of workspace with each pressure change. In addition, CT delivers ionizing radiation to the body and thus its use is limited. Both imaging techniques can be impractical to combine with surgical procedures. Furthermore, both imaging techniques may be prone to overestimation.

The apparatus may be configured to measure insufflation gas flow through the input conduit (e.g. trocar) and estimate the volume by integrating the flow. In this way, the estimation of the rate of change of the volume can be obtained.

Gas leaks can introduce an error which is proportional to the integration time. The apparatus may be configured to reduce the integration time before and after the change in insufflation pressure. In this way, more accurate results may be obtained.

Advantageously, the mechanical properties of the system can be determined or estimated based on the forced oscillations. In this technique, a sinusoidal stimulus at a low frequency, e.g. 0.1 to 40 Hz, may be provided and the resulting flow can be measured. The transfer function pressure versus flow at the frequency of the stimulus can return a complex number, wherein the real part of the complex number is a resistance of the internal cavity, and the imaginary part represents the reactance of the internal cavity. The reactance has two components, namely compliance and inertia. At lower frequencies compliance may be predominant, and at higher frequency inertia may be predominant.

A sinusoidal pressure waveform with a small amplitude can be imposed onto the generated insufflation pressure and the relative flow can be measured at the inlet, e.g. at the input conduit or at the inlet of the trocar. The volume can be determined accurately while being less sensitive to leaks.

Additionally or alternatively, a forced oscillating pressure may be provided and the resulting acceleration of the skin of the body at different anatomical landmarks such as on the abdomen and on the back may be measured. The detected response in the form of accelerations can be used for the assessment of mechanical behavior of the internal cavity. The acceleration measured, for instance on the skin of the body, depends on the mechanical properties of the pathway of the pressure waveform. The phase shift of pressure versus acceleration is less prone to noise and calibration error than the gain of the signal.

The physical properties (e.g. elasticity) of the internal cavity can be determined in various ways by imposing a forced oscillatory input and measuring a response of the internal cavity to the forced oscillatory input. Different types of responses can be measured for this purpose. The insufflator gas pressure (cf. input) can be controlled on the basis of the determined physical properties of the internal cavity.

Figure 8:
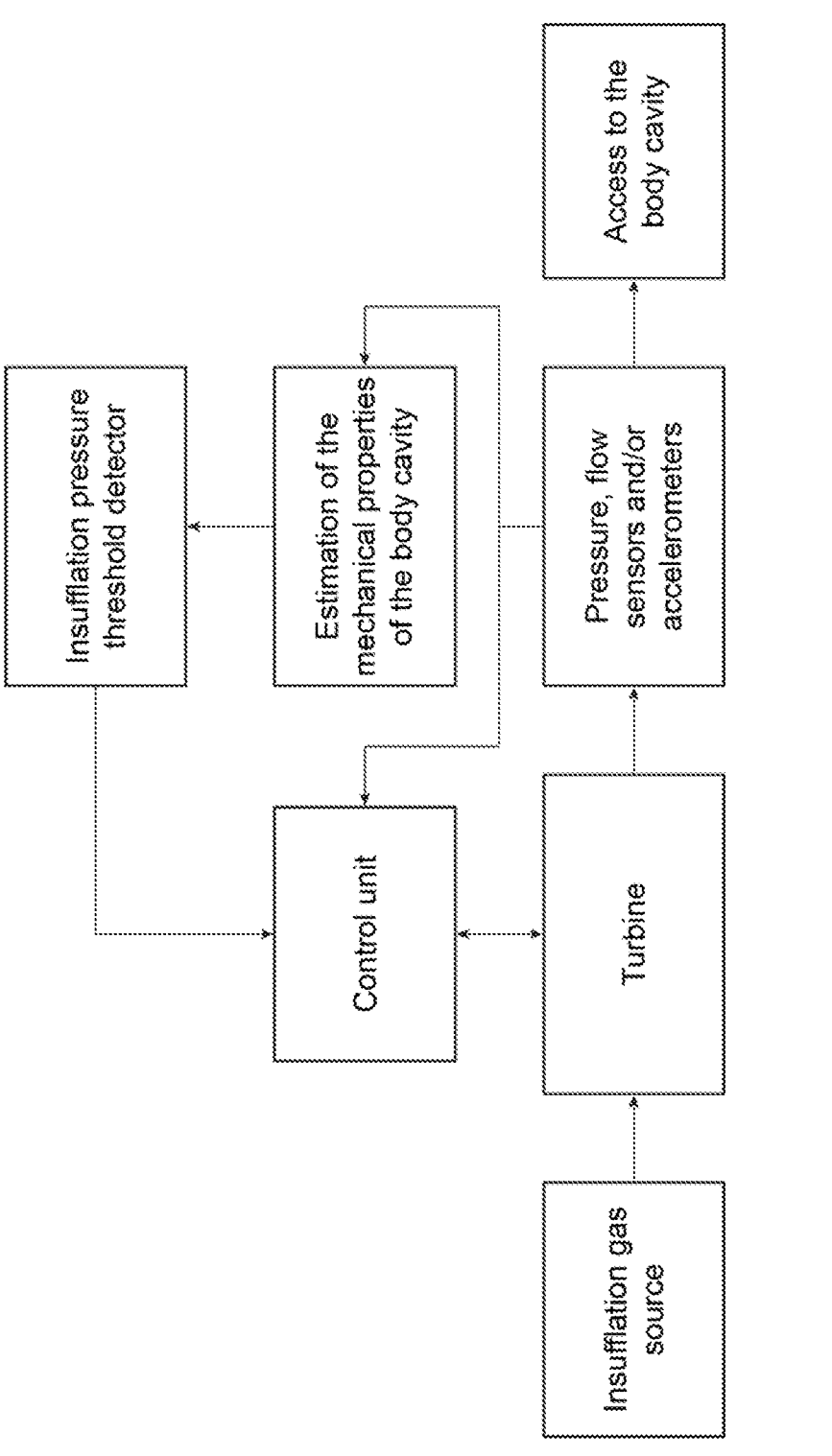
FIG. 8 shows a schematic block diagram of an apparatus.

FIG. 8 shows another schematic block diagram of an apparatus 1. In this embodiment, the apparatus includes a turbine. The turbine may be servo-controlled. The turbine receives a low pressure insufflation gas from a source that could be a tank connected to a pressure regulator and an expansion chamber (for example an elastic balloon) or any other device. The expansion chamber can be coupled to a heater to avoid the administration of cold insufflation gas. The gas source may be able to provide heated, moisturized, depressurized insufflation gas at a flow rate sufficient to produce the pressure perturbation.

The velocity of the turbine can be modulated in order to provide a constant pressure (the insufflation pressure) with an overimposed pressure perturbation.

In case of use of a sinusoidal pressure waveform, the frequency of the sinusoidal pressure may range from 0.1 Hz to 20 Hz or in a preferred embodiment from 0.5 to 15 Hz. The amplitude of the oscillation range may range from 1 to 4 $cmH_2O$ peak to peak and preferably from 2 to 3 $cmH_2O$ peak to peak.

Pressure and flow sensors may be placed on the insufflation line connecting the pressure generator to the input conduit which provides access to the confined volume of the internal cavity.

Additionally or alternatively, a flow sensor can be used to estimate the mechanical properties of the cavity, a pressure sensor provides feedback to the control unit on the insufflation pressure in order to change the control action of the turbine to match the targeted pressure.

Additionally or alternatively, accelerometers applied on the skin of the patient can be used to detect body surface displacement.

In the shown embodiment, only the turbine of the apparatus is utilized for generating the insufflator pressure. In this way, the complexity of the device can be significantly reduced.

Figure 9:
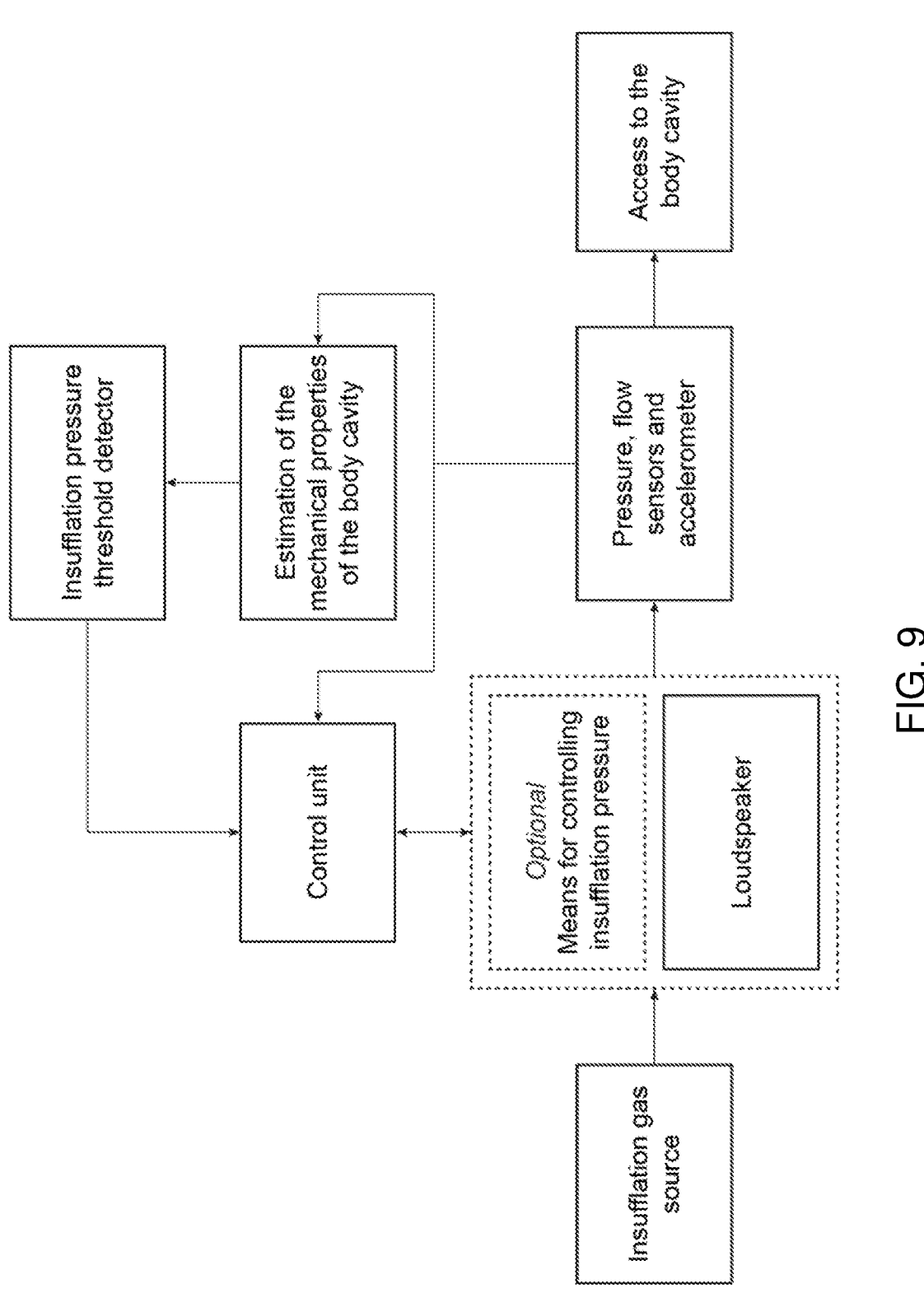
FIG. 9 shows a schematic block diagram of an apparatus.

FIG. 9 shows another schematic block diagram of an apparatus 1. In this embodiment, the apparatus includes a loudspeaker for estimation of the mechanical properties of the internal cavity 3. The loudspeaker can produce the pressure stimulus at the desired frequencies to estimate the mechanical properties of the internal cavity. As the loudspeaker is not able to produce a constant positive insufflation pressure, a pressure generator is also needed. Pressure, flow sensors and/or accelerometers can be used to estimate the physical/mechanical properties of the internal cavity by means of the forced oscillations as described above.

It will be appreciated that other means for generating the pressure perturbations can also be employed. For instance, the apparatus may include a moving piston configured to generate the perturbation pressure. In an advantageous embodiment, a turbine may be used which can provide better control over the imposed forced pressure oscillations.

Figure 10:
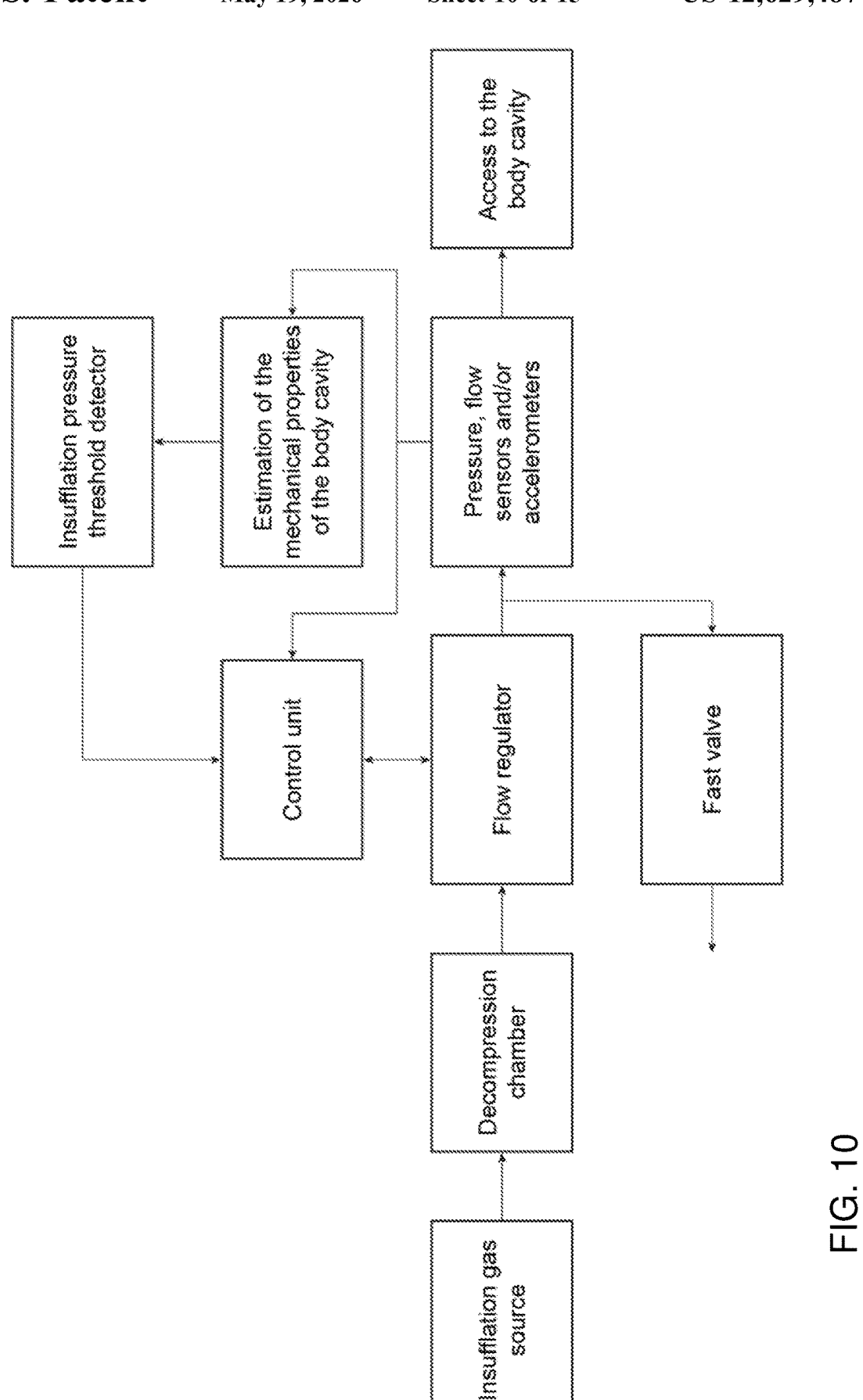
FIG. 10 shows a schematic block diagram of an apparatus.

FIG. 10 shows another schematic block diagram of an apparatus 1. The apparatus 1 can be arranged to perform a modulation of bias flow of insufflation gas. The gas may come from a source such as a tank. The gas can be decompressed in a chamber and a controlled flow can be applied to the internal cavity 3 through the input conduit 7. The insufflation gas can be output (and removed actively or passively) through a modulating valve electrically controlled the outlet of the insufflation line. The resistance offered by this valve to insufflation gas flow can be electrically modulated in order to obtain the desired combination of insufflation and perturbation pressure. The valve may be configured to produce the oscillations. A voice coil valve may for example be suitable to produce the oscillations. Other types of valves may also be suitable. Insufflation gas flow may be kept as low as possible by using a suitable valve able to generate the desired pressure with the aim of minimizing the insufflation gas dispersed to the surroundings.

The apparatus 1 may include a signal generator near the cavity. The pressure perturbation may be performed near the cavity, potentially in the device that also contains the sensory components. This can for example be a trocar which provides access to the cavity.

Figure 11:
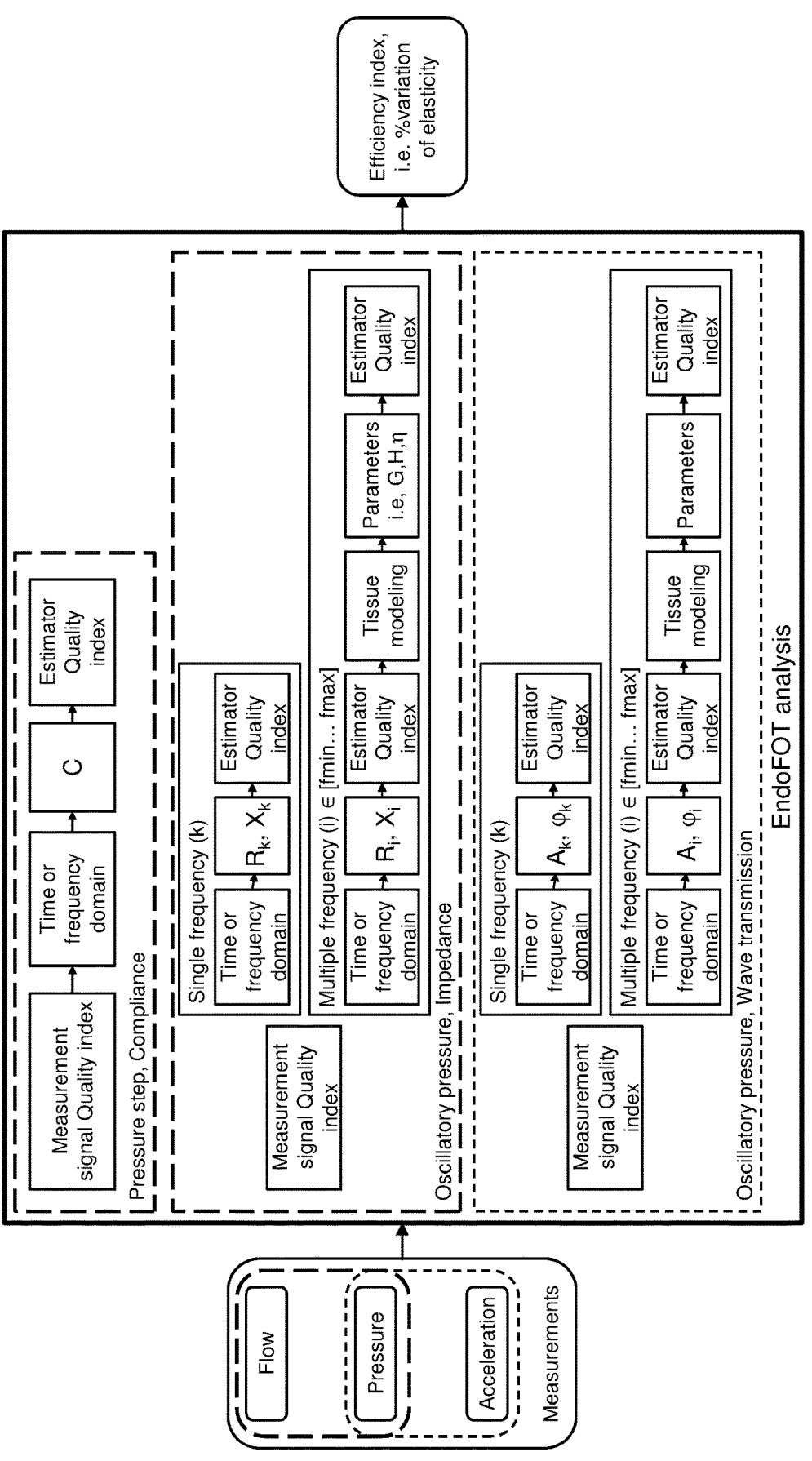
FIG. 11 shows a schematic block diagram of an endoscopic forced oscillation analysis.

FIG. 11 shows a schematic block diagram of an endoscopic forced oscillation analysis. An overview of exemplary measurement, analysis and characterization of the mechanical conditions of the endoscopic cavity is depicted. The to be characterized physical properties of the internal cavity can be estimated by comparing the forced signal input and the measured output. An exemplary flowchart of an analysis method is provided.

The apparatus 1 may be arranged for estimating/determining mechanical properties of the body cavity by using the forced oscillations by means of the insufflator. By employing the forced oscillations more information on the biomechanical properties of the endoscopic internal cavity can be obtained by means of the apparatus. This information can be subsequently used for optimization of the insufflator pressures applied during the endoscopic procedure. The mechanical properties could be characterized in multiple ways, such as for example mechanical compliance, mechanical impedance and/or pressure wave transmission.

For the characterization of the compliance or impedance of the internal cavity, flow can be considered as the output. In the case of analyzing the pressure wave transmission, the acceleration can be considered to be the output.

The measurement signal quality index may be calculated. The quality index may be calculated before analyzing the measured results. The type of index used to determine the quality can depend on the signal used. For instance step signals, periodic signals (both single and multi-frequency) and impulse signals can be used. After determining the quality of the measured signal, the analysis can take place in either the time or frequency domain. The quality of the estimated parameter can be described with the estimator quality index. The result of this analysis could be an efficiency index (compared to a baseline measurement at a certain level of pressure) or the value of the parameter itself. In the case of using multi-frequency signals, additional modeling can be applied to obtain more parameters to describe the properties of the surgical workspace. When a model is used to estimate additional parameters, an additional quality estimator can be used for describing the quality of the estimator model.

Pressure and flow measurements can be used for estimation of the compliance of the internal cavity within the time domain. Mechanical compliance is defined as $C=\Delta V/\Delta P$. The applied step in pressure will give a certain amount of flow. The change in volume, $\Delta V$, can be estimated by numerical integration of the flow data. The resulting stroke volume can be divided by the applied pressure amplitude to estimate the compliance.

Additionally or alternatively, reactance of the internal cavity may be estimated. The apparatus may be configured to generate sinusoidal forcing pressure at several frequencies that can be applied either one at a time or over-imposed to one another. Accordingly, it is possible to estimate the impedance of the system, which is frequency dependent, at a single frequency or at the stimulus frequencies. In order to estimate frequency response, it is possible to use spectral approaches or least square methods.

Impedance can be split into a real and an imaginary part, wherein the imaginary part is the reactance of the internal cavity. If only one frequency is used, reactance can be immediately used as input for the efficiency index, otherwise reactance estimated at several frequencies can be furtherly fitted on model describing tissue properties such as the constant phase model.

Parameters within the frequency domain can be estimated using pressure and flow measurements. The frequency response model can be function fitted onto the estimated impedance using a least squares error estimator. The constant phase model can be used to estimate the resistance, inductance, elastance and the tissue damping of the internal cavity. The ratio between the elastance and tissue damping can be defined to be the parameters. This approach enables to describe the reactive mechanics of the internal cavity.

Additionally or alternatively, a waveform transmission can be determined using the forced oscillations. By applying well known time or frequency-domain based algorithms such as cross correlation or spectral analysis it is possible to estimate the amplitude ratio and phase shift between the input signal and the output signal that depends on the mechanical properties of the tissues even though it may not provide an immediate physical interpretation. This can be done, as in case of pressure and flow for a single frequency or on a range of frequencies.

Figure 12:
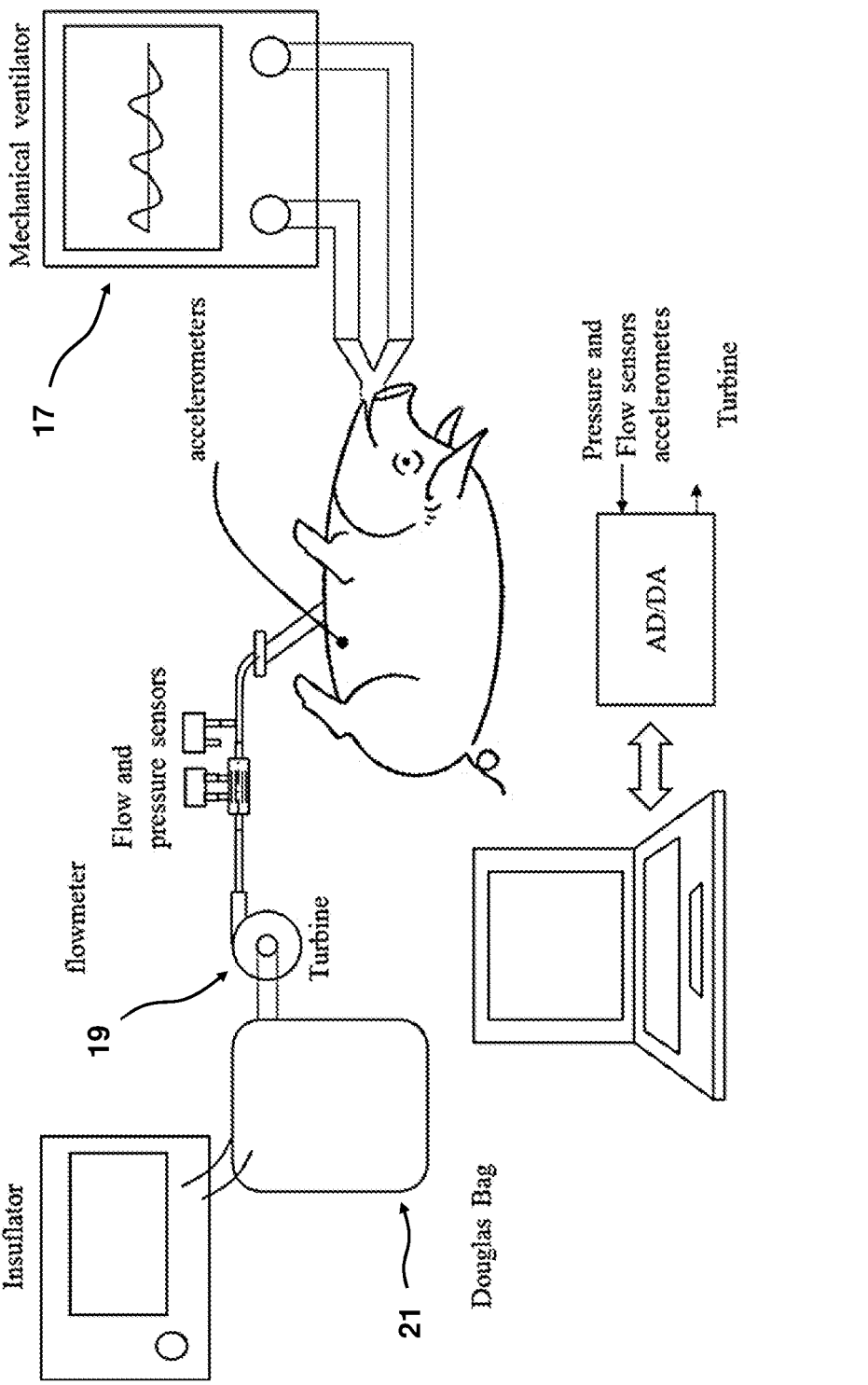
FIG. 12 shows a schematic diagram of an apparatus.

FIG. 12 shows another schematic diagram of an apparatus 1. In this exemplary embodiment, the apparatus is employed for insufflating an internal cavity (not lungs) of a pig. The apparatus may also be suitable for use with other animals or humans.

Physical properties (e.g. compliance and/or impedance) of the insufflated internal cavity can be monitored by endoscopic application of the forced oscillations. The apparatus can be configured to apply oscillatory pressure perturbations and measure the effects in terms of pressure and/or flow.

The subject is mechanically ventilated using a breathing device 17. Every pressure step may require some time in order to allow stabilization of the elastic and viscoelastic response of the internal cavity. The remaining time may be used to probe the frequency response of the subject during an expiratory hold to avoid interaction with the breathing pattern. Forced oscillation frequencies may for example range from 0.5 to 15 Hz with an amplitude of for example 2 cmH20 peak to peak. The forced oscillations may for instance be at a frequency of 0.5, 1, 2, 3, 5, 10 and 15 Hz. Other values of the frequencies and amplitudes are also possible, depending on the subject and the specific internal cavity (e.g. for assessing the abdominal internal cavity). Optionally, a CT scan may be employed to assess the abdominal volume.

In the shown example, the apparatus includes a turbine 19. A brush less motor may be arranged for operating the turbine 19. The inlet of the turbine may be connected to a commercial insufflator that provides the needed flow of $CO_2$. A Douglas bag 21 may be added along the lines connecting the insufflator to the turbine 19 to provide a $CO_2$ reservoir. Proximal measurements of pressure and flow may be added. In this example, an accelerometer is fixed on the abdomen of the pig along the midline.

The index, reporting the variation of the elastic properties compared to the variation in the first step, can be estimated as:

$$C(i) = \frac{C(i+1) - c(i)}{C(1) - C(0)}$$

with i=pressure values, C=mechanical compliance or can be derived from the reactance X at low frequency:

$$C \sim \left| \frac{1}{X} \right|$$

Figure 13:
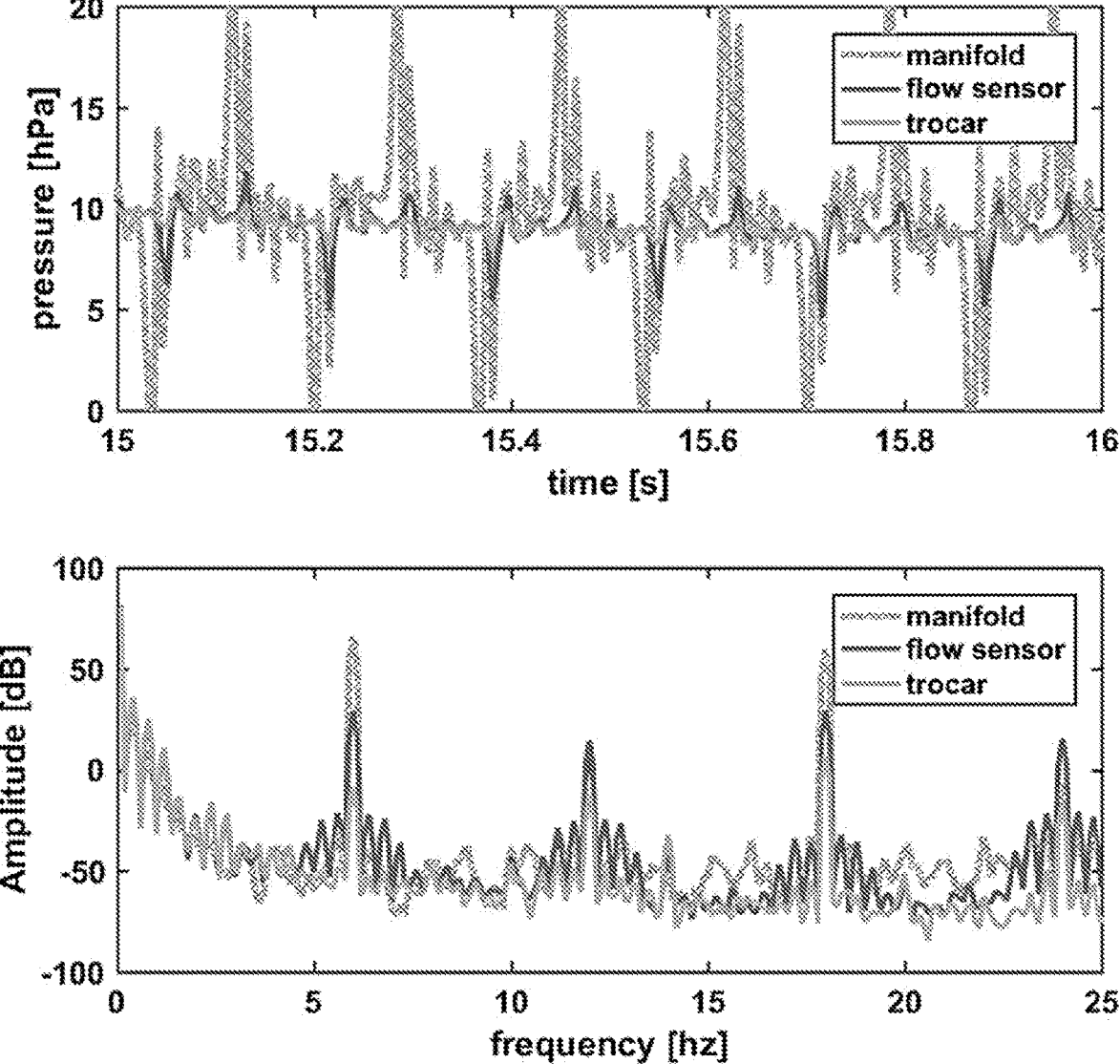
FIG. 13 shows graphs of pressure versus time and amplitude versus frequency.

FIG. 13 shows graphs of pressure versus time and amplitude versus frequency. The forced pressure signal can dampen throughout the body. At the input conduit the peak-to-peak amplitude is larger than 20 hPa. An amplitude reduction can be caused by the insufflation tube and sensor. Harmonic distortions are present, these harmonics can be seen in the spectral density plot. The second harmonic has roughly the same amplitude.

Closed-loop controllers can be used to create the required forced pressure signal, this enhances the signal quality. Using a closed-loop controlled power source and a flow sensor with a lower impedance can obviate the need for manual adjustment of the forced pressure amplitude and correction of frequency behaviour of the flow sensor.

FIG. 14 shows resistance and reactance versus frequency obtained using the apparatus 1. As shown in FIG. 2, an analogy exists between the pneumatic and electrical domain, impedance Z=p/V̇=U/I, with p being pressure, V̇ being flow, U being electric voltage, and I being electric current. Surgical workspace compliance can be described by an electrical capacity. The mass (M) of the gas in the workspace can be described by an inductor L.

A resistor inductor capacitor model, or RLC-model, can be used for determining physical properties of the internal cavity 3 by employing the forced oscillations on the internal cavity 3 defining the confined volume 5. The RLC-model can describe the frequency behaviour as a result of resistance, inertia and compliance. This model holds for higher frequencies when used with the apparatus according to the invention. The resistance $R_{ws}$ is frequency independent and the ratio between the inertia and capacitance can be used to describe the reactance $X_{ws}$. The capacitance is related to the surgical workspace compliance.

$$Z_{ws}(\omega) = R_{ws} + I_{ws} j\omega + \frac{1}{C_{ws} j\omega}$$

Figure 14A:
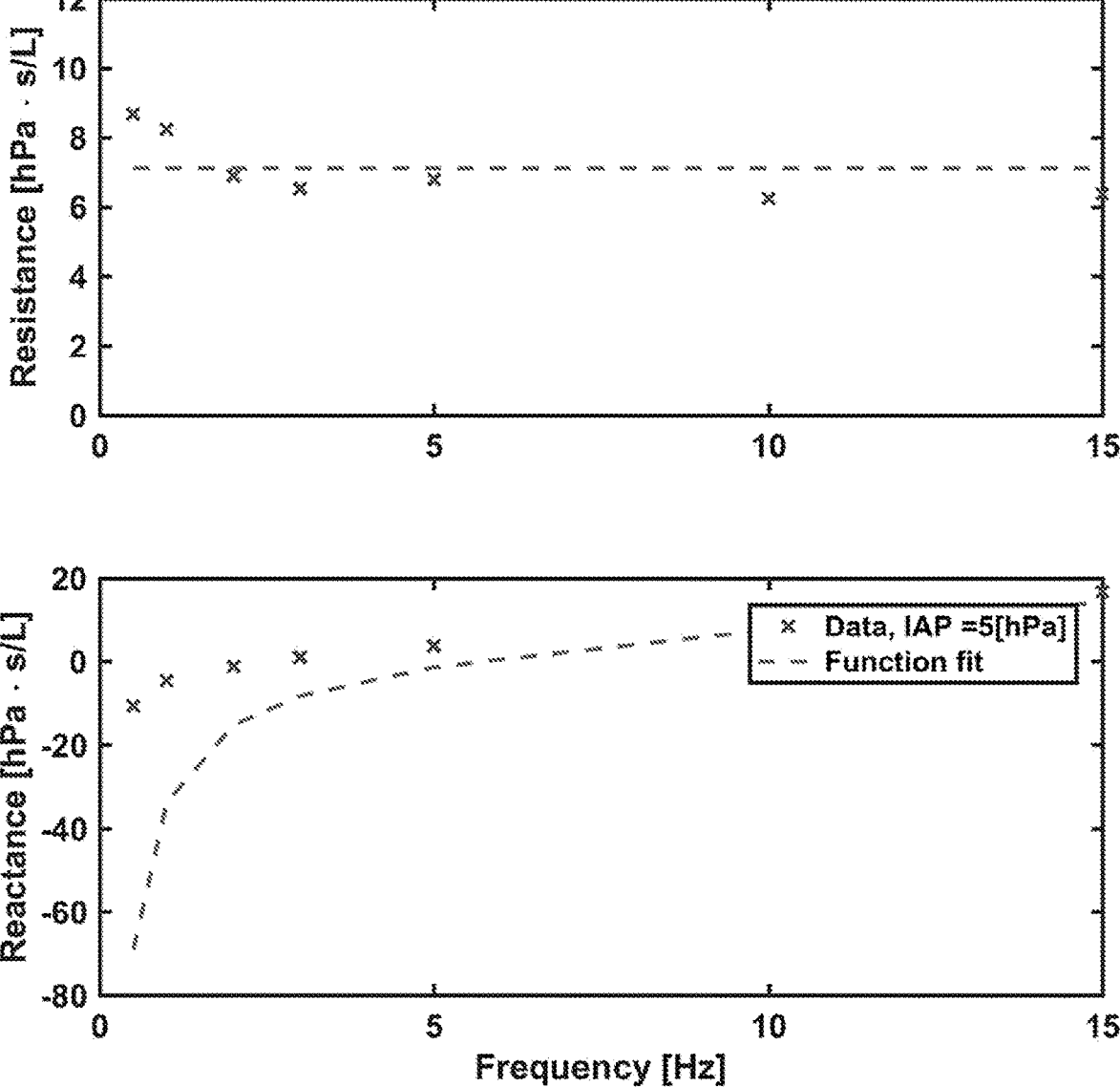
FIG. 14 (A and B) shows resistance and reactance versus frequency.

Function fitting this model onto the retrieved response data can provide the parameters describing the behaviour of the internal cavity at a certain intra-abdominal pressure. The internal cavity forms a confined volume defining the surgical workspace. These parameters can be affected by the applied pressure. An exemplary function fitting of the RLC-model onto acquired experimental data is shown in FIG. 14A.

There may exist some deviation between the model and the fitted acquired data. It can be seen from the frequency behaviour of the surgical workspace that at higher frequencies the error seems smaller. At low frequencies the resistance/damping appears to be higher. The behaviour of the low frequency reactance seems to be well-presented yet shifted, which may be the result of a hysteresis effect.

The RLC-model can be adapted or replaced by a model able to describe the low frequency behaviour while leaving the high frequencies untouched. This may be achieved by employing a constant phase model, wherein the hysteresis effects are included in the model without altering the phase of the model.

At high frequencies the behaviour of the RLC-model is dominated by the R and L parameters. The last term, is used to describe the low frequency behaviour. The $G_{ws}$ includes the tissue resistance/damping effects. It only affects the resistance plot. The $(-H_{ws} j)$ term describes the elastance/stiffness. It is divided by $\omega$ to reduce these effects at high frequencies ($\omega=2\pi f$). Although $R_{ws}$ and $X_{ws}$ are plotted separately, they are dependent. The ratio between $G_{ws}$ and $H_{ws}$ provides information on the hysteresis. The constant phase model is given by:

$$Z_{ws}(\omega) = R_{ws} + I_{ws} j\omega + \frac{G_{ws} - H_{ws} j}{\omega^\alpha}$$

$$\alpha = 2/\pi \cdot \tan^{-1}\left(\frac{H_{ws}}{G_{ws}}\right)$$

The hysteresivity is given by:

$$\eta = \frac{G_{ws}}{H_{ws}}$$

Figure 14B:
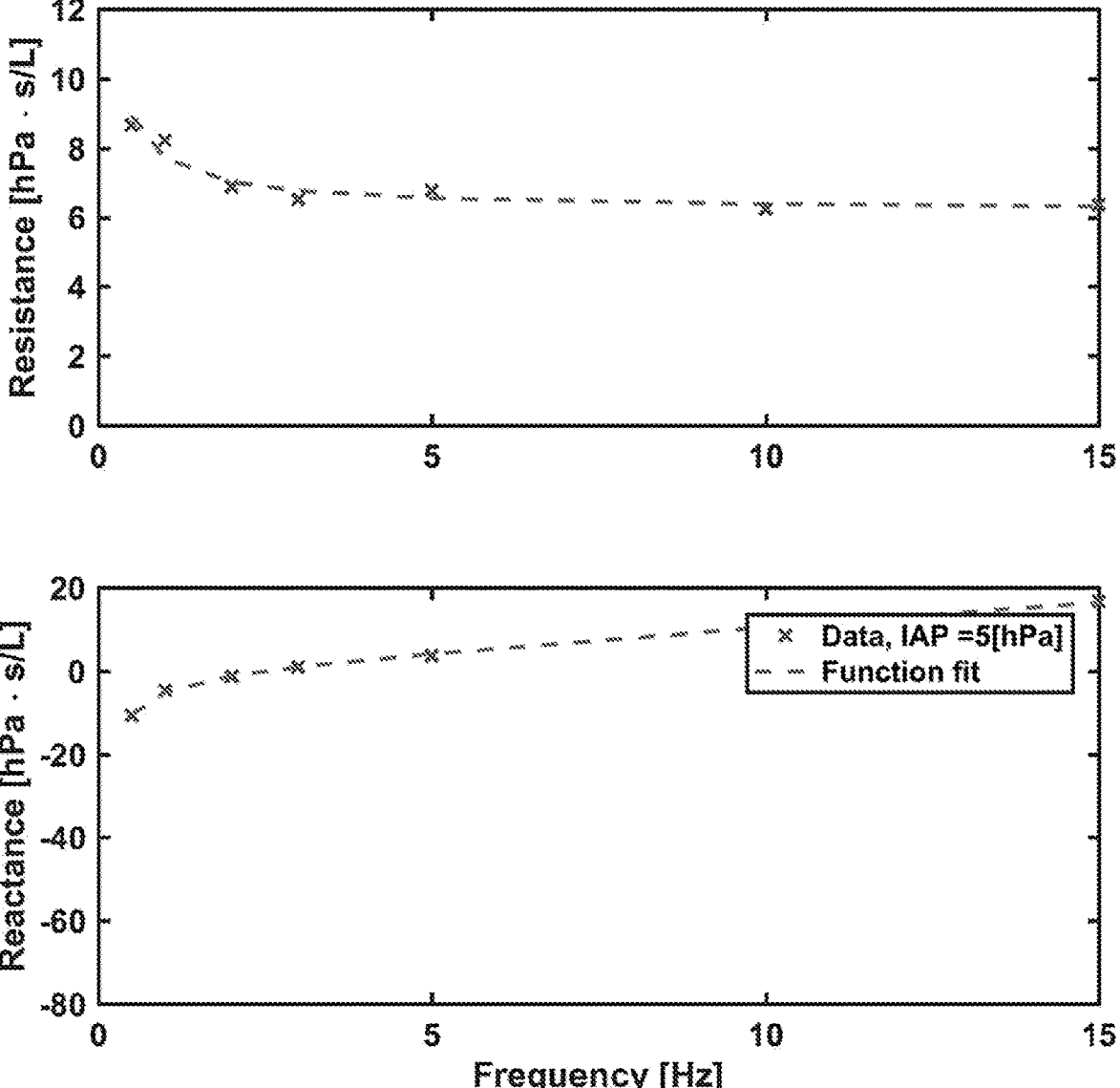

The results of plotting this improved model are shown in FIG. 14B. It can be seen that the model describes the data a lot better than the RLC-model. Hence, the constant phase model may provide a more accurate way of describing the mechanical behaviour of the internal cavity 3 resulting from the forced oscillations.

At low frequencies, the signal may be distorted. At these frequencies, the flow may become decoupled from the pressure that has been applied. The decoupling may become worse when the intra-abdominal pressure is increased. The function fit may be improved when these frequencies are not included.

A better estimation of resistance ($R_{ws}$) and Inertia ($I_{ws}$) can be obtained by discarding one or more frequencies. Also a better estimation of elastance ($H_{ws}$) may be possible in this way.

It will be appreciated that forced oscillations applied to the airways (lungs) is typically at frequencies of 5 Hz and higher (up to 20 Hz), yet applying it within internal body cavities (e.g. insufflation for endoscopy) like the thorax and abdomen can require frequencies that are lower.

The features described above are examples of various concepts, and they may be modified in any desired manner. For example, various elements and steps may be divided, combined, rearranged, omitted, and augmented as desired. The various elements may be implemented using computer components, such as processors and computer readable memories, and any of the elements described herein may be implemented using software, hardware, or any combination of the two.

Various embodiments may be implemented using hardware elements, software elements, or a combination of both. Examples of hardware elements may include processors, microprocessors, circuits, application specific integrated circuits (ASIC), programmable logic devices (PLD), digital signal processors (DSP), field programmable gate array (FPGA), logic gates, registers, semiconductor device, microchips, chip sets, et cetera. Examples of software may include software components, programs, applications, computer programs, application programs, system programs, machine programs, operating system software, mobile apps, middleware, firmware, software modules, routines, subroutines, functions, computer implemented methods, procedures, software interfaces, application program interfaces (API), methods, instruction sets, computing code, computer code, et cetera.

Herein, the invention is described with reference to specific examples of embodiments of the invention. It will, however, be evident that various modifications, variations, alternatives and changes may be made therein, without departing from the essence of the invention. For the purpose of clarity and a concise description features are described herein as part of the same or separate embodiments, however, alternative embodiments having combinations of all or some of the features described in these separate embodiments are also envisaged and understood to fall within the framework of the invention as outlined by the claims. The specifications, figures and examples are, accordingly, to be regarded in an illustrative sense rather than in a restrictive sense. The invention is intended to embrace all alternatives, modifications and variations which fall within the spirit and scope of the appended claims. Further, many of the elements that are described are functional entities that may be implemented as discrete or distributed components or in conjunction with other components, in any suitable combination and location.

In the claims, any reference signs placed between parentheses shall not be construed as limiting the claim. The word 'comprising' does not exclude the presence of other features or steps than those listed in a claim. Furthermore, the words 'a' and 'an' shall not be construed as limited to 'only one', but instead are used to mean 'at least one', and do not exclude a plurality. The mere fact that certain measures are recited in mutually different claims does not indicate that a combination of these measures cannot be used to an advantage.

The invention claimed is:

1. An insufflator apparatus for exposing structures within an internal cavity of an animal or human subject body, the internal cavity forming a confined volume within the subject body, the apparatus comprising:

an input conduit for exchanging gas with the confined volume;

a gas insufflator for insufflation of gas into the confined volume through the input conduit, wherein the gas insufflator is configured to provide an insufflator gas pressure to the confined volume, wherein the gas insufflator is configured to impose at least one pressure or flow oscillation to obtain a forced oscillating pressure or flow delivered to the confined volume, and wherein the forced oscillating pressure or flow has at least one component with a frequency that differs from a respiratory frequency of the subject body;

a monitor configured to monitor a response of the internal cavity, to the forced oscillating pressure or flow, for determining one or more tissue stress properties of the internal cavity in response to the imposed pressure or flow oscillation; and an adapter configured to adjust, based on the determined one or more tissue stress properties of the internal cavity, the insufflator gas pressure or flow.

2. The apparatus according to claim 1, wherein the adapter is configured to receive at least one property of the one or more tissue stress properties of the internal cavity from the monitor, including at least one property taken from the group consisting of:

a mechanical impedance, a mechanical resistance, a mechanical reactance, a compliance, an elastance, and a visco-elastic tissue elastance and damping.

3. The apparatus according to claim 1, wherein the adapter is configured to keep the insufflator gas pressure or flow below a threshold.

4. The apparatus according to claim 3, wherein the monitor is configured to determine a rate threshold based on one or more of the determined one or more tissue stress properties of the internal cavity.

5. The apparatus according to claim 1, wherein the forced oscillating pressure or flow includes a plurality of frequency components.

6. The apparatus according to claim 1, wherein the gas insufflator further includes:

a pressure sensor coupled to the input conduit for measuring the forced oscillating pressure within the confined volume, and/or a flow sensor coupled to the input conduit for measuring the insufflator gas flow to the confined volume, wherein the monitor is configured to determine the response of the internal cavity by measuring insufflator gas pressure and/or insufflator gas flow during application of forced oscillating gas pressure.

7. The apparatus according to claim 1, wherein the gas insufflator includes or is coupled to a gas turbine pump for generating at least one pressure or flow oscillation to obtain a forced oscillating pressure or flow delivered to the confined volume.

8. The apparatus according to claim 1, wherein the respiratory frequency of the subject body is a lung ventilation frequency imposed by a ventilator delivering a therapeutic respiratory pressure to the respiratory system of the animal or human subject body.

9. The apparatus according to claim 1, wherein the monitor is configured to determine one or more tissue stress properties of the internal cavity on a periodic basis for monitoring changes in one or more tissue stress properties of the internal cavity, and wherein the adapter is configured to dynamically adjust the insufflation pressure and/or flow based on changes in the one or more tissue stress properties of the internal cavity.

10. The apparatus according to claim 1, wherein the insufflator is arranged to generate, in proximity to the input conduit, a variable pressure, and wherein the variable pressure has:

a peak to peak amplitude equal to or less than 10 hPa, and a frequency in a range of 0.1-100 Hz.

11. The apparatus according to claim 1, wherein the gas insufflator is configured to perform a mean distending pressure sweep during the application of the oscillating pressure.

12. The apparatus according to claim 1, wherein the gas insufflator is configured to perform a frequency sweep of the forced oscillating pressure.

13. The apparatus according to claim 1, wherein one or more tissue stress properties of the internal cavity are estimated by model fitting.

14. The apparatus according to claim 1, wherein the gas insufflator includes a trocar as an input mechanism arranged for being sealingly inserted in the internal cavity of the animal or human subject body.

15. A method of controlling an insufflator apparatus for exposing structures within an internal cavity of an animal/human subject body, the internal cavity forming a confined volume within the animal or human subject body, wherein the apparatus includes an input conduit constructed to exchange gas with the confined volume, a gas insufflator for insufflation of gas into the confined volume through the input conduit, the gas insufflator constructed to deliver an insufflator pressure to the confined volume, the method including:

imposing, using the gas insufflator, at least one gas pressure or gas flow oscillation to obtain a forced oscillating gas pressure or gas flow provide to the confined volume, the forced oscillating pressure or flow having at least one preset component with a frequency that differs from a respiratory frequency of the subject body;

monitoring, using a monitor, a response by the internal cavity to the forced oscillating gas pressure or gas flow for determining one or more tissue stress properties of the internal cavity in response to the imposed pressure or flow oscillation; and adjusting, using an adapter and based on the determined one or more tissue stress properties of the internal cavity, an insufflation pressure or flow.

16. The method according to claim 15, wherein the adapter is configured to receive at least one property of the one or more tissue stress properties of the internal cavity from the monitor, including at least one property taken from the group consisting of:

a mechanical impedance, a mechanical resistance, a mechanical reactance, a compliance, an elastance, and a visco-elastic tissue elastance and damping.

17. The method according to claim 15, wherein the adapter is configured to keep the insufflator gas pressure or flow below a threshold.

18. The method according to claim 17, wherein the monitor is configured to determine a rate threshold based on one or more of the determined one or more tissue stress properties of the internal cavity.

19. The method according to claim 15, wherein the forced oscillating pressure or flow includes a plurality of frequency components.

20. The method according to claim 15, wherein the gas insufflator further includes:

a pressure sensor coupled to the input conduit for measuring the forced oscillating pressure within the confined volume, and/or a flow sensor coupled to the input conduit for measuring the insufflator gas flow to the confined volume, wherein the monitor is configured to determine the response of the internal cavity by measuring insufflator gas pressure and/or insufflator gas flow during application of forced oscillating gas pressure.

* * * * *